United States Patent [19]
Fielding et al.

[11] Patent Number: 5,922,554
[45] Date of Patent: Jul. 13, 1999

[54] INHIBITION OF CELLULAR UPTAKE OF CHOLESTEROL

[75] Inventors: Christopher J. Fielding; Phoebe E. Fielding, both of Mill Valley, Calif.

[73] Assignee: The Regents of the University of California, Oakland, Calif.

[21] Appl. No.: 08/740,444

[22] Filed: Oct. 29, 1996

Related U.S. Application Data

[60] Provisional application No. 60/008,079, Oct. 30, 1995.

[51] Int. Cl.$^6$ ...................................................... C12Q 1/60
[52] U.S. Cl. .................................. 435/11; 435/4; 436/71; 552/544
[58] Field of Search ........................... 435/4, 11; 436/71; 552/544

[56] References Cited

PUBLICATIONS

McCloskey et al., Biochimica et Biophysica Acta, vol. 921: 320–332, Jan. 1987.
Shechter et al., J. of Lipid Research, vol. 22, 63–71, Jan. 1981.
Bretscher & Munro (1993) *Science* 261:1280–1281.
Castro & Fielding, *Biochemistry*, 27:25–29 (1988).
Chege & Pfeffer (1990) *J. Cell Biol.*, 111:893–899.
Conrad et al. (1995) *J. Cell Biol.* 131:1421–1433.
Coxey et al. (1993) *J. Lipid Res.*, 34:1165–1176.
Cullis & Hope (1991) In *Biochemistry of Lipids, Lipoproteins and Membranes* (Vance, D. E. & Vance, J., Eds) pp. 1–41, Elsevier Press, Amsterdam.
Cupers et al. (1994) *J. Cell Biol.*, 127:725–735.
Dupree et al. (1993) *EMBO J.*, 12:1597–1605.
Emmelot et al., (1964) *Biochim. Biophys. Acta* 90:126–145.
Fielding et al., *Biochemistry*, 30:8551–8557 (1991).
Fielding & Fielding (1986) *J. Biol. Chem.*, 261:5233–5236.
Fielding et al., *Proc. Natl. Acad Sci. (USA)* 81:2512–2516 (1984).
Fielding (1992) *FASEB J.*, 6:3162–3168.
Fielding & Fielding (1981) *Proc. Natl. Acad. Sci. (USA)*, 78:3911–3914.
Francone et al. (1990) *J. Lipid Res.*, 31:2195–2200.
Furuchi et al. (1993) *J. Biol. Chem.*, 268:27345–27348.
Goldstein & Brown, (1974) *The Journal of Biological Chemistry*, 249:5153–5162.
Goldstein et al., *Proc. Natl. Acad. Sci. (USA)*, 75:1877–1881 (1978).
Goldstein et al. (1985) *Ann. Rev. Cell Biol.* 1:1–39.
Gottlieb et al. (1993) *J. Cell Biol.* 120:695–710.
Hansen et al. (1993) *J. Cell Biol.*, 121:61–72.
Havel et al., *J. Clin. Invest.*, 34:1345–1353 (1954).
Helder & Boyett (1978) *J. Lipid Res.* 19:514–518.
Hokland et al., *J. Biol. Chem.*, 268:25343–25349 (1993).
Huang et al. (1993) *Arterioscler. Thromb.*, 13:445–458.
Johnson et al. (1991) *Biochim. Biophys. Acta*, 1085:273–298.
Kawano et al. (1993) *Biochemistry*, 32:5025–5028).
Ktistakis et al. (1992) *Nature*, 356:344–346.
Lange, *J. Biol. Chem.*, 269:3411–3414 (1994).
Larkin et al., (1983) *Cell* 33:273–285.
Miida et al., *Biochemistry*, 29:10469–10474 (1990).
Montesano et al. (1982) *Nature*, 296:651–653.
Oram et al., *Arterioscler. Thromb.*, 11:403–414 (1991).
Pearse (1976) *Proc. Natl. Acad. Sci. USA* 73:1255–1259.
Pearse & Robinson (1990) *Ann. Rev. Cell Biol.* 6:151–171.
Pedersen & Carafoli, *Trends Biochem. Sci.*, 12:146–150 (1987).
Pfeffer (1991) *Cell Biophys.* 19:131–140.
Reaven et al. (1986) *J. Clin. Invest.*, 77:1971–1984.
Rothberg (1995) *Meth. Enzymol.* 250:669–679.
Rothman & Schmit (1986) *Cell*, 46:5–9.
Steck et al. (1988) *J. Biol. Chem.*, 263:13023–13031.
Steinman et al., (1976) *J. Cell Biol.* 68:665–687.
Suckling & Stange, *J. Lipid Res.*, 26:647–671 (1985).
Tagaya et al., *J. Biol. Chem.*, 268:2662–2666 (1993).
Thyberg & Moskalewski (1992) *J. Cell Sci.*, 103:1167–1175.
Voyno–Yasenetskaya et al., *Proc. Natl. Acad Sci. (USA)*, 90:4256–4260 (1993).
Woodman & Warren (1991) *J. Cell Biol.*, 112:1133–1141.

*Primary Examiner*—Christina Y. Chan
*Assistant Examiner*—Patrick Nolan
*Attorney, Agent, or Firm*—Townsend and Townsend and Crew LLP

[57] ABSTRACT

This invention provides for methods of reducing cholesterol uptake by a cell. The invention is premised in part on the discovery of a new mechanisms by which free cholesterol (FC) is internalized into a cell from low-density lipoproteins. Inhibition of this mechanism reduces the internalization of free cholesterol into cholesterol transport vesicles thereby reducing free cholesterol content of the cell at physiological concentrations of LDL and HDL.

12 Claims, 13 Drawing Sheets

INHIBITION OF CELLULAR UPTAKE OF CHOLESTEROL

CROSS-REFERENCE TO RELATED APPLICATIONS

This is a continuation-in-part of U.S. Ser. No. 60/008,079, filed on Oct. 30, 1995, which is herein incorporated by reference for all purposes.

This invention was made with Government support under National Institutes of Health Public Health Service Grant No: 14237-2. The Government has certain rights in this invention.

FIELD OF THE INVENTION

This invention relates to the regulation of cellular free cholesterol. More specifically, this invention relates to the discovery of a metabolic pathway that mediates the transport of free cholesterol (from low-density lipoproteins LDLs), to intracellular compartment (e.g. to a free cholesterol transport vesicle (CTV)). Inhibition of this pathway decreases the internalization of free cholesterol thereby reducing total cellular cholesterol content.

BACKGROUND OF THE INVENTION

Uptake of cholesterol by cells of the blood vessel wall is an integral part of heart disease (atherosclerosis). Cholesterol-filled cells ("foam cells") burst and die, attracting scavenger cells, promoting an inflammatory reaction and contributing to the fatty part of the atherosclerotic plaque which may eventually break off or form a focus-promoting thrombosis.

In other pathological conditions including diabetes, thyroid hormone deficiency, renal failure and some inherited hyperlipidemias, LDL free cholesterol is unusually high, while HDL levels are markedly reduced. This suggests that abnormal regulation of cellular uptake of cholesterol is a component in the etiology of these disease states.

Cellular free cholesterol levels are normally well buffered against changes in external (serum) concentrations of lipoprotein free cholesterol (FC) through a variety of influx and efflux mechanisms (Fielding (1992) *FASEB J.*, 6: 3162–3168). High affinity low-density lipoprotein (LDL) receptor-mediated endocytosis represents one important mechanism for the regulation of cellular sterol. However, in most nonhepatic cells these receptors are markedly down-regulated by even the low concentrations of LDL typical in normal plasma. Similarly, the synthesis of new cholesterol (Goldstein et al., *Proc. Natl. Acad. Sci. (USA)*, 75: 1877–1881 (1978)) is also down-regulated by low concentrations of LDL. Thus, neither receptor-mediated endocytosis nor cholesterol synthesis appear to be important mechanisms in cholesterol regulation by most mammalian cells.

A third mechanism, selective transfer of esterified cholesterol (EC) from LDL has been demonstrated (Reaven et al. (1986) *J. Clin. Invest.*, 77: 1971–1974), but this pathway seems to be active mainly on steroidogenic cells. Despite the low rates of cholesterol uptake via these pathways, high rates of FC efflux, unaccounted for by these mechanisms, continue to be observed in the presence of plasma lipoproteins (Fielding & Fielding (1981) *Proc. Natl. Acad. Sci. (USA)*, 78: 3911–3914; Johnson et al. (1991) *Biochim. Biophys. Acta*, 1085: 273–298; Kawano et al. (1993) *Biochemistry*, 32: 5025–5028). These considerations suggest there is substantial recycling of FC between the cell surface and the extracellular medium.

Several laboratories have observed that the efflux of FC from peripheral cells to medium (e.g., serum) lipoprotein acceptors is primarily to high-density lipoproteins (HDL) (Francone et al. (1990) *J. Lipid Res.*, 31: 2195–2200; Huang et al. (1993) *Arterioscler. Thromb.*, 13: 445–458). The origin of this free cholesterol (FC) and the mechanism by which it may have originally entered the cell have been little studied, even though it could be a significant contributor to cholesterol homeostasis. Each of the major plasma lipoproteins (HDL, LDL and very low-density lipoprotein, VLDL) is a potential source of FC for influx. Simple diffusion, or molecular collision accounts for the transfer of cholesterol between lipoproteins and erythrocytes (Steck et al. (1988) *J. Biol. Chem.*, 263: 13023–13031; Johnson et al. (1991) *Biochim. Biophys. Acta*, 1085: 273–298). However, additional mechanisms seem likely to contribute in fibroblasts, vascular smooth muscle cells and macrophages. In these cells (unlike erythrocytes) efflux is markedly inhibited by protease pretreatment of the cell surface (Kawano et al. (1993) *Biochemistry*, 32: 5025–5028).

SUMMARY OF THE INVENTION

The present invention relates to the discovery of a new metabolic pathway that mediates the uptake of free cholesterol from low-density lipoproteins and its ultimate transport from the plasma membrane to an intracellular compartment. This pathway, designated herein the low-density lipoprotein free cholesterol (LDL-FC) pathway, is a low affinity high capacity cholesterol transport pathway. Free cholesterol is selectively taken up from LDLs substantially without accompanying protein or other lipid. The free cholesterol thus taken up is ultimately incorporated (sequestered) in an intracellular compartment, more particularly into a "cholesterol transport vesicle" where it may ultimately be esterified. The LDL-FC pathway is inhibited by vesicular ATPase inhibitors such as N-ethylmaleimide (NEM), nitrate ion (e.g., $KNO_3$), and bafilomycin. The LDL-FC pathway is also inhibited by cytochalasin and monensin. The LDL-FC pathway is not inhibited by cAMP inhibitors such as isobutyl methylxanthine (IBMX) or forskolin, or ATPase inhibitors such as azide, vanadate, or progesterone or by inhibitors of Golgi-mediated protein transport (e.g., brefeldin A, vinblastine, and taxol). The LDL-FC vessicle formation is not inhibited by nocodazole (e.g., at up to 60 $\mu M$ concentration), however transport of the vessicles to the plasma membrane is inhibited.

Inhibition of the LDL-FC pathway reduces the production of cholesterol transport vesicles thereby reducing intracellular cholesterol store and thus the total cholesterol content of the cell. Thus, in one embodiment, this invention provides a method of inhibiting cholesterol uptake by a cell. The method involves inhibiting the internalization of free cholesterol from the plasma membrane of the cell into a cholesterol transport vesicle. The method preferably involves inhibiting a vesicular ATPase. The vesicular ATPase is preferably inhibited by contacting the cell with a compound that binds the vesicular ATPase at an ATP binding region, more preferably a binding region selected from the group consisting of LLYGPPGCGKTLLAR-(SEQ ID NO:1) and LFYGPPGCGKTLLAK-(SEQ ID NO:2). The method can preferably involve contacting the cell with NEM or nitrate (e.g., $KNO_3$). Virtually any nucleated mammalian cell is suitable, with human cells being more preferred and fibroblasts, human vascular smooth muscle cells, human vascular (e.g., aortic) endothelial cells, macrophages, hemapoietic cells, liver, kidney, and human intestinal mucosal cells being most preferred.

In another embodiment, this invention provides a method of identifying an agent that blocks or enhances the transport of free cholesterol from the plasma membrane to a cholesterol transport vesicle (i.e. an agent that blocks or enhances the LDL-FC transport pathway). The method involves contacting the cell with the agent in the presence of low-density lipoprotein and quantifying the amount of free cholesterol internalized by the cell. In a preferred embodiment, the low-density lipoprotein comprises a labeled cholesterol (e.g. $^3$H-FC-LDL). Quantification then can comprise detecting the labeled cholesterol in the cell. In another embodiment, the quantification can comprise quantifying the amount of a cholesterol transport vesicle produced by the cell. Suitable cells include, but are not limited to, any of the cells described above.

In still yet another embodiment, this invention provides for an isolated cholesterol transport vesicle. The transport vesicle is produced by a cell and the vesicle is enriched for free cholesterol such that the vesicle has a density that ranges from about 1.05 g/ml to about 1.12 g/ml, more preferably from about 1.06 g/ml to about 1.10 g/ml and most preferably from about 1.07 g/ml to about 1.09 g/ml. The vesicle is one whose production by the cell is inhibited by contacting the cell with NEM or nitrate ion (e.g. $KNO_3$). The vesicle is also one whose production by the cell is not substantially inhibited by contacting the cell with forskolin, isobutylmethylxanthine, progesterone, azide or vanadate. The vesicle is similarly one whose formation is not substantially inhibited by inhibitors of Golgi-mediated protein transport (e.g., brefeldin A, vinblastine, taxol at up to 60 $\mu$M concentration) or by inhibitors of inhibits microtubule-dependent transport (e.g., nocodazole). The vesicle can incorporate a labeled cholesterol provided from a lowdensity lipoprotein in a medium that contacts the cell. The vesicle can be derived from virtually any mammalian cell, more preferably a human cell, and most preferably any of the cells identified herein.

Finally, in another embodiment, this invention provides a method of detecting abnormal lipid uptake by a cell. The method involves placing the cell in media comprising known concentrations of high-density lipoproteins (HDLs) and low-density lipoproteins (LDLs) and quantifying the uptake of free cholesterol from the LDLs by the cell. The low-density lipoprotein can comprise a labeled cholesterol. The quantification can be by any method known to one of skill in the art, and more preferably is by one of the methods described herein.

DEFINITIONS

The following abbreviations are used herein: LDL, low-density lipoprotein; HDL, high-density lipoprotein; FC, free cholesterol; EC, esterified cholesterol; NEM, N-ethylmaleimide.

Free cholesterol is cholesterol that is not esterified to a fatty acid chain, but rather exists as the free alcohol. In contrast, esterified cholesterol (EC) is cholesterol that is joined (esterified) to a fatty acid.

"Substantial inhibition" of the LDL-FC pathway, or of cholesterol transport vesicle formation, by a particular agent, refers to a significant decrease in the influx of free cholesterol or in the formation of cholesterol transport vesicles by a cell contacted with that agent as compared to the same type of cell under the same conditions, but in the absence of the agent. Substantial inhibition is at least about 50% decrease, preferably at least about a 60% decrease, more preferably at least about a 70% a decrease and most preferably at least about an 80% decrease in free cholesterol influx (e.g. as measured by the transport of labeled FC from LDLs) or in the rate of formation or the amount of cholesterol transport vesicles.

Lipoproteins are complexes or compounds containing lipid and protein. Lipoproteins are found in plasma and have been historically characterized by their flotation constants (densities) with low density lipoproteins (LDLs), ranging from about 1.019 g/ml to about 1.063 g/ml, and high density lipoproteins (HDLs), ranging from about 1.063 g/ml to about 1.21 g/ml. However, more recently it has been recognized that, particularly in various pathological conditions the lipid composition may vary and LDLs and HDLs can deviate from these ranges. Thus, LDLs and HDLs are also characterized in terms of the principle protein. LDLs typically contain apolipoprotein B as the only, or as the principle (greater than 50% of the protein content of the lipoprotein) protein of the LDL. In contrast, HDLs contain apolipoprotein A-I as the only, or principle protein, of the lipoprotein.

The term "internalization" when used in reference to free cholesterol, refers to the transport of free cholesterol from the external plasma membrane of the cell into the cytoplasm. Typically internalization involves invagination of the plasma membrane and subsequent formation of a vesicle. The cholesterol thus internalized may be in the form of free cholesterol (FC) or it may be esterified (EC).

The term "cholesterol transport vesicle", as used herein, refers to a vesicle whose production is mediated by the LDL-FC cholesterol transport pathway. The formation of cholesterol transport vesicles is inhibited by vesicular ATPase inhibitors such as N-ethylmaleimide (NEM) and nitrate ion (e.g., $KNO_3$), but not by forskolin, isobutyl methylxanthine, progesterone, azide, or vanadate. The formation of cholesterol transport vesicles of this invention is also inhibited by hyperosmotic media, reduction or elimination of $K^+$, cytochalasin, monensin, or bafilomycin, but not by brefeldin A, vinblastine, nocodazole, or taxol (e.g., at up to 60 $\mu$M concentration). The cholesterol transport vesicles may store cholesterol either as free cholesterol (FC) or as esterified cholesterol (EC). Because the cholesterol transport vesicles are enriched for cholesterol, as compared to other intracellular membranes, the transport vesicles have a reduced density ranging from about 1.05 g/ml to about 1.12 g/ml, more preferably from about 1.06 g/ml to about 1.10 g/ml and most preferably from about 1.07 to about 1.09 g/ml. Cholesterol transport vesicles can be readily identified by placing cells in media containing labeled LDL free cholesterol and then detecting the presence of the label in the vesicles as described herein.

A vesicle is said to be "enriched" for free cholesterol when the concentration of free cholesterol of the vesicle is greater than that of other types of vesicles found in the cell or is greater than that of the region of the plasma membrane from which the vesicle originates. In the instant case, cholesterol transport vesicles originate from coated pits; areas of the plasma membrane that contain virtually no free cholesterol and yet the transport vesicles contain more cholesterol than other vesicle types found within the cell. Vesicles so enriched can be distinguished from other vesicles and intracellular membranes by the fact that, due to the higher cholesterol content, the enriched vesicles have a lower density and therefore float at a higher point in a density gradient than other intracellular membranes.

The term "cholesterol uptake" as used herein refers to the net accumulation or loss of cholesterol by a cell. As explained herein, cells acquire cholesterol from low-density lipoproteins and lose cholesterol to high-density lipoproteins. In addition, cells sequester cholesterol in an intracellular compartment (e.g., the cholesterol transport vesicle) via the LDL-FC pathway of this invention. As the cholesterol content of the plasma membrane is tightly regulated, an increase in cholesterol internalization leads to an increase in total cellular cholesterol (an increase in cholesterol uptake), while, conversely, a decrease in cholesterol internalization leads to a decrease in total cellular cholesterol (a decrease in cholesterol uptake).

The term "caveolae" refers to the clathrin-free surface invaginations shown in intact cells by electron microscopy to be rich in Free cholesterol, sphingolipids and GPI-anchored proteins. Caveolar free cholesterol is uniquely accessible to cholesterol oxidase in unfixed cells. Caveolin, a lipid binding protein, has been shown to be associated with caveolae in several cell lines, including fibroblasts, and in caveolar membrane fractions purified from these cells.

The terms "isolated" "purified" or "biologically pure" refer to material which is substantially or essentially free from components which normally accompany it as found in its native state.

The term "detectable label" is used herein to refer to any composition detectable by spectroscopic, photochemical, biochemical, immunochemical, electrical, optical or chemical means. Such labels include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Preferred detectable labels, for use in this invention, do not alter the cellular processing of the compound to which they are bound. Thus, preferred free cholesterol labels do not alter transport of free cholesterol by the LDL-FC pathway of this invention. Similarly, preferred labels do not substantially alter the gross physical properties of the labeled component. In particular, preferred labels do not substantially alter the density of the lipid to which they are joined. Thus, radioactive labels (e.g., $^3$H, $^{125}$I, $^{35}$S, $^{14}$C, or $^{32}$P) are most preferred for use in the present invention.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

DETAILED DESCRIPTION

Figure 1:
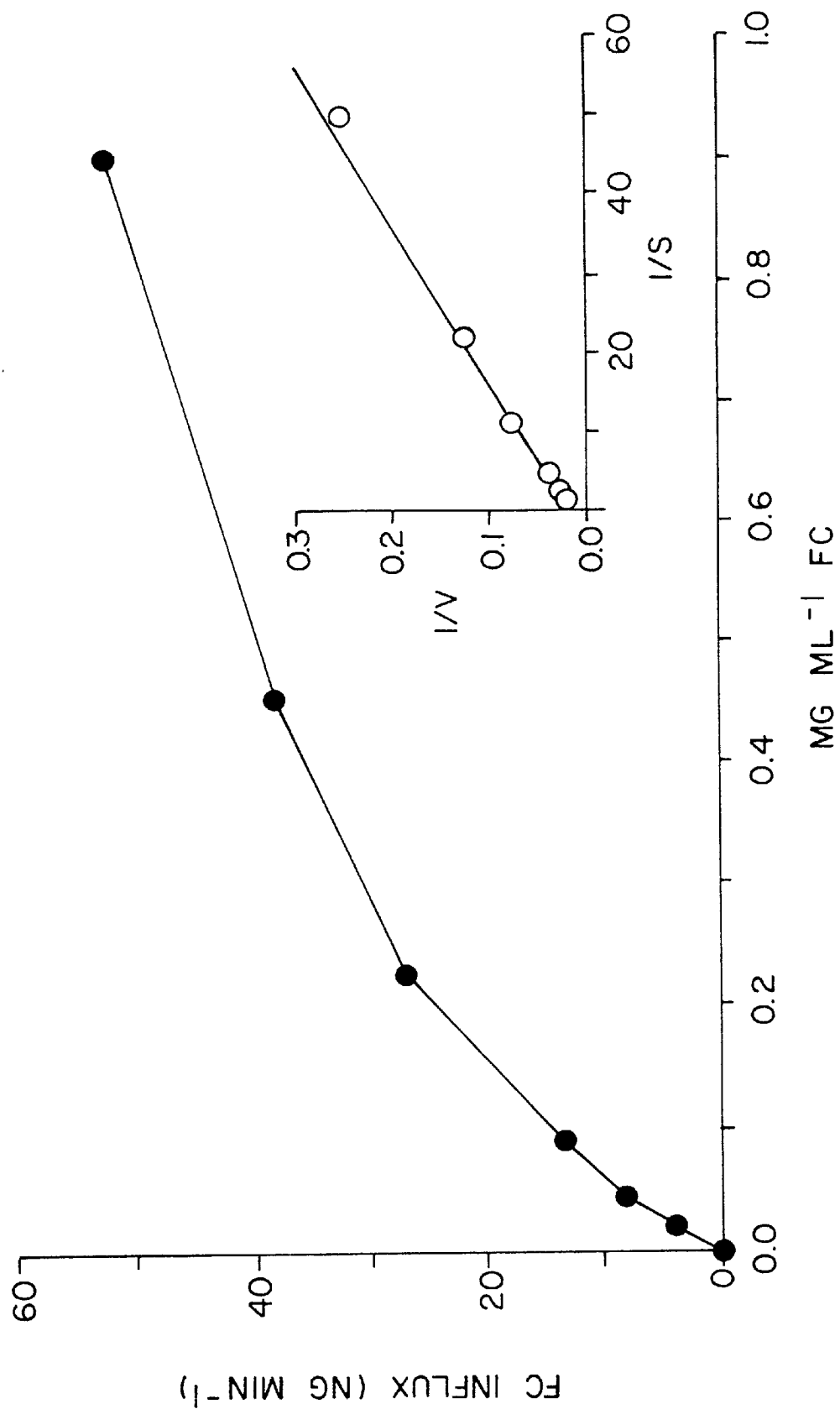
FIG. 1 illustrates the concentration dependence of LDL $^3$H-FC uptake by fibroblast monolayers. Unlabeled monolayers equilibrated with 7% plasma-DMEM were washed with PBS (×4), incubated (10 min, 37° C.) with LDL at the indicated concentration, then washed with PBS-albumin (4 mg ml$^{-1}$), then with PBS (×4). The washed monolayers were then extracted as described herein and cell-associated label determined. Each data point represents the mean of triplicate dishes. Insert: double reciprocal plot of the experimental data.

This invention relates to the discovery of a new pathway by which free cholesterol (FC) from low-density lipoproteins (LDLs) is bound and preferentially (selectively) internalized by mammalian cells. This pathway (designated herein as the LDL-FC pathway) accounts for a major part of the free cholesterol influx required to maintain free cholesterol levels in the plasma membrane in response to the high level of free cholesterol efflux (mainly to high-density lipoproteins HDLs) under normal physiologic conditions. This pathway is thus an important component in the regulation of cellular cholesterol levels and abnormal function of this pathway is believed to result in pathological states characterized by abnormal cellular cholesterol levels. Conversely, manipulation of this pathway, e.g., by the administration of drugs that up-regulate or down-regulate FC internalization, offers a previously unknown and unsuspected approach to the treatment of such pathologies.

This invention thus, provides for new methods of inhibiting cholesterol uptake by a cell where the methods involve inhibiting the LDL-FC pathway described herein. In another embodiment, this invention provides methods of identifying agents that block or enhance the transport of free cholesterol from the plasma membrane to a cholesterol transport vesicle. This invention also provides for isolated cholesterol transport vesicles. In addition this invention provide methods of detecting abnormal lipid uptake by a cell where the methods involve quantifying the uptake of free cholesterol from LDLs.

I. The LDL-FC Transport Pathway

The low-density lipoprotein free cholesterol (LDL-FC) pathway of this invention is a low affinity, high capacity cholesterol transport pathway by which free cholesterol is selectively taken up from LDLs substantially without accompanying protein or other lipid. The free cholesterol thus taken up is ultimately incorporated (sequestered) in an intracellular compartment, more particularly into a "cholesterol transport vesicle" where it may ultimately be esterified. The high cholesterol uptake capacity provided by this pathway indicates that it an important component in cellular regulation of cholesterol.

In properties and mechanism the LDL-FC pathway of this invention differs substantially from previously described lipid-transport pathways. For example, in one previously known pathway, the intact LDL, including LDL cholesterol, LDL protein, and LDL esterified cholesterol, was endocytosed in toto (Goldstein et al., *Ann. Rev. Cell. Biol.*, 1: 1–39 (1985)). In contrast, the LDL-FC pathway of this invention, the free cholesterol uptake was selective and almost unaccompanied by the uptake of LDL protein or LDL cholesteryl ester mass. Unlike receptor-mediated endocytosis, the LDL-FC pathway was similar in normal fibroblasts and several lines of LDL receptor-deficient cells. Finally, in contrast to receptor-mediated endocytosis which is a high affinity low capacity pathway, the LDL-FC pathway of this invention is a low-affinity, high capacity pathway whose rate varies strongly with medium LDL levels over the physiological range.

Both the LDL-FC pathway of this invention and the receptor mediated endocytosis pathway are inhibited by heparin. It is unlikely this represents a similarity between the two pathways, but, without being bound to a particular theory, probably reflects, in each case, formation of soluble charged complexes of LDL and heparin which are less reactive with the cell surface.

Consistent with observations reported herein in Example 1, Slotte et al., *Biochem. J.*, 222: 821–824 (1984), reported uptake and esterification of LDL-FC label by LDL receptor-deficient fibroblasts. However, this study only addressed LDL-FC uptake in abnormal (receptor deficient) cells. In addition, no measurement was made of cellular FC mass, was made, no inhibition of LDL-FC incorporation was observed and no mechanism of selective LDL-FC incorporation was identified.

The LDL-FC transport pathway of this invention does not reflect the simple exchange of cholesterol at the cell surface, for several reasons. There was a marked increase in cellular FC mass in the absence of HDL; indeed LDL-FC was retained in the cells almost quantitatively. Influx was largely LDL concentration dependent while efflux was HDL concentration dependent. In addition, there was an obvious lag (10 min) between the binding of labeled LDL-FC and its availability for efflux to HDL.

The effects of metabolic inhibitors also confirmed that the LDL-FC influx pathway of this invention differs from other mechanisms of FC transport. In human hepatoblastoma (HepG2) cells, progesterone promoted the transfer of FC from the plasma membrane to the interior of the cell (Lange, *J. Biol. Chem.*, 269: 3411–3414 (1994)). In contrast, progesterone was without effect on influx via the LDL-FC pathway of this invention. Similarly, as was chloroquine, an inhibitor of lysosomal transport that blocks endocytotic processing had no effect on cholesterol influx via the LDL-FC pathway. The transfer of newly-synthesized cholesterol to the plasma membrane of fibroblasts is cAMP-dependent and stimulated by forskalin and IBMX (Hokland et al., *J. Biol. Chem.*, 268: 25343–25349 (1993)), while LDL-FC influx was unaffected by these agents. Finally, LDL-FC influx was blocked by inhibitors specific for an ATPase now broadly implicated in vesicular transport in both yeast and mammalian cells (Pederson & Carafoli, *Trends Biochem. Sci.*, 12: 146–150 (1987); Sollner et al., *Nature*, 362: 318–324 (1993); Ferro-Novick & Jahn, *Nature*, 370: 191–193 (1994)).

ATPases in this family are characterized by resistance to azide and vanadate, and sensitivity to nitrate and NEM. The best-characterized of these enzymes (NEM-sensitive factor, NSF) forms a complex at the inner surface of the plasma membrane with attachment factors and other proteins (Weidman et al., *J. Cell. Biol.*, 108: 1589–1596 (1989)) and plays an essential role in the transfer of solute vesicles between intracellular compartments. ATPases with similar properties have been reported within the plasma membrane.

In LDL-FC transfer, the effect of NEM and $KNO_3$ was to prevent the transfer of free cholesterol away from the plasma membrane to the cell interior. As a result, most of the FC transferred to the cells from LDL remained accessible to plasma lipoproteins, and the initial rate of efflux of FC from prelabeled cells to plasma was increased several-fold. Without being bound to a particular theory, it is believed that the role of the NEM-sensitive factor in LDL-FC influx is to draw free cholesterol into specific plasma membrane microdomains from which it can be either interiorized or effluxed to HDL.

II. Inhibition of the LDL-FC Transport Pathway

Because of its high capacity, and sensitivity to the physiological LDL concentration range, the LDL-FC transfer pathway of this invention is effective as part of a mechanism to stabilize plasma membrane free cholesterol concentration as low-density lipoprotein concentration and the free cholesterol content of LDLs changes in response to nutritional status. Under pathological conditions, including thyroid hormone deficiency, diabetes, renal failure and some inherited hyperlipidemias, LDL free cholesterol content is unusually high (Fielding, *J. Lipid. Res.*, 25: 1624–1628 (1984); Bagdade et al., *Arteriosclerosis*, 10: 232–239 (1990); Dieplinger et al., *J. Clin. Invest.*, 77: 1071–1083 (1986))) while HDL levels are markedly reduced. Changes of this kind in plasma lipoproteins are often associated with an accumulation of both free and esterified cholesterol in the vascular bed.

In addition, uptake of cholesterol by cells of the blood vessel wall is an integral part of heart disease (atherosclerosis). Cholesterol-filled cells ("foam cells") burst and die, attracting scavenger cells, promoting an inflammatory reaction and contributing to the fatty part of the atherosclerotic plaque which may eventually break off or form a focus promoting thrombosis.

One of skill in the art would appreciate that treatments that reduce net cholesterol uptake by a cell, and therefore cellular cholesterol content, would thereby mitigating one aspect of these pathologies. Thus, in one embodiment, this invention provides for a method of net cholesterol uptake by a cell, said method comprising inhibiting the internalization of free cholesterol from the plasma membrane into the cytoplasm, more particularly into a cholesterol transport vesicle. The method simply involves contacting the cell with a composition that inhibits the LDL-FC pathway of this invention. As illustrated in Example 1, inhibition of the LDL-FC pathway (e.g., by treatment with NEM or $KNO_3$) results in an almost complete (>80%) inhibition of the uptake of free cholesterol from LDLs (see, FIG. 8). Example 2 illustrates inhibition of the LDL-FC pathway of this invention by production of a hyperosmotic environment, reduction or elimination of $K^+$ (e.g., by replacement in the media with $Na^+$), by the inhibition of actin polymerization (e.g., through the use of cytochalasin, by the inhibition of ATPase-driven acidification (e.g., though the use of bafilomycin, and by the use of monensin.

III. Characterization of Inhibitors

As described above, NEM and $KNO_3$ are known inhibitors of vesicular ATPases. The pattern of inhibition of the LDL-FC transport mechanism is characteristic of a vacuolar-type (or vesicular type) ATPase with a cysteine residue located within a Wood type A ATP-binding sequence. Clathrin-free uncoated pits contain a single reported ATPase inhibited by NEM/$KNO_3$ (N-ethylmaleimide-sensitive protein, NSF), while clathrin-coated pits contain two structural ATPases sensitive to sensitive to $KNO_3$ and NEM; an $H^+$-ATPase responsible for acidification in compartment of uncoupling of receptor and ligand (CURL) and an ATPase of unknown function (VCP, valosin containing protein). VCP and NSF contain virtually identical ATP binding regions:

NSF: -$L_{265}$LYGPPGCGKTLLAR-(SEQ ID NO:1)

VCP: -$L_{515}$FYGPPGCGKTLLAK-(SEQ ID NO:2)

$C_{272}$ has been identified in NSF as the binding site for NEM which mediates the inhibition of vesicular transport (Whiteheart et al., *J. Cell. Biol.*, 126: 945–954 (1994)). This structure is absent in $H^+$-ATPase, where NEM binds to a different ATP-binding sequence (Feng et al., *J. Biol. Chem.*, 269: 13224–13230 (1994)).

Preferred inhibitors for use in this invention are NEM-like ATPase inhibitors that bind one or more cysteines within the ATP binding site of the target vesicular ATPase or vesicular ATPase-like mediator of the LDL-FC pathway. Preferred inhibitors can be identified by their ability to bind the ATP-binding sequences described above, or homologous ATP-binding sequences. Alternatively, suitable inhibitors can be identified simply by screening for the ability of the putative inhibitor to inhibit the selective uptake of free cholesterol from LDLs as described below in section IV.

IV. Screening for LDL-FC Inhibitors or Inducers

This invention also provides methods of screening for inhibitors and inducers of LDL-FC uptake. In a preferred embodiment, the methods involve contacting a cell with a test compound in the presence of low-density lipoprotein and measuring the uptake of free cholesterol by the cell as compared to a similar (control) cell measured without exposure to the test compound. An increase of free cholesterol incorporated into the treated cells as compared to the control cells indicates the test compound has agonistic activity, while conversely, a decrease of detectable label incorporated into the treated cell as compared to the control cell indicates an inhibitory activity.

Preferred test cells include, but are not limited to, virtually any nucleated mammalian cell, with human cells being more preferred and fibroblasts, human vascular smooth muscle cells, human vascular (e.g., aortic) endothelial cells, macrophages, hemapoietic cells, liver, kidney, and human intestinal mucosal cells being most preferred.

In one embodiment, the free cholesterol of the LDL is labeled with a detectable label, and the uptake of free cholesterol is detected by detecting (quantifying) the amount of detectable label incorporated into the cell either as a function of time, or at a fixed time after exposing the cell to the label and the test compound. An example of one such assay is provided in Example 1(J) where the uptake of $^3$H-FC is measured in the presence of NEM or $KNO_3$ (see, e.g. FIG. 8).

Alternatively, the agonistic or antagonistic activity of a compound can be determined screened simply by measuring changes in the rate of production, or the absolute concentration, of free cholesterol transport vesicles in cells exposed to the compound as compared to control cells similarly treated but without the test compound. test cells in the presence and absence of the compound that is to be tested. Methods of isolating free cholesterol transport vesicles are provided below in Section VI. Once the vesicle is isolated the lipid can be quantified according to any of a number of methods well known to those of skill in the art (see, e.g., Example 1).

One of skill will readily appreciate that assays of the type describe herein are subject to numerous variations. Thus, for example, in a competitive format, the same assays can be used to identify compounds that block agents known to up- or down-regulate the LDL-FC pathway of this invention. In such competitive formats, the cells are contacted with two agents; one agent known to up- or down-regulate the LDL-FC pathway and a second agent whose activity is to be screened. The ability of the second agent to mitigate the agonistic or antagonistic activity of the known agent is then measured as described above.

The ambient LDL and HDL concentrations can be altered to up-regulate or to down-regulate the LDL-FC pathway to provide a characteristic level of LDL-FC pathway against which to compare assay the agonistic or antagonistic effect of the agents to be tested. Thus, for example, where it is desired to up-regulate the LDL-FC pathway, the test cells are preferably cultured in media and/or plasma containing high concentrations of LDL (e.g., about 1.0 mg/ml protein), but low concentrations of HDL (e.g., about 0.25 mg/ml protein). Conversely, where it is desired to down-regulate the LDL-FC pathway, the cells are preferably cultured in media and/or plasma containing low concentrations of LDL (e.g., about 0.25 mg/ml protein) and high concentrations of HDL (e.g., about 1.5 mg/ml protein).

V. Assays for LDL-FC Pathway Activity

As indicated above, alteration of cellular cholesterol levels is indicative of a number of pathologies (e.g. diabetes, thyroid hormone deficiency, renal failure and inherited hyperlipidemias, etc.). In such cases it is desirable to ascertain whether abnormal cholesterol content is a consequence of the cholesterol processing by the tissue exhibiting the abnormality or simply a response to abnormal plasma lipid content (e.g., abnormal HDL:LDL ratio). Thus, this invention provides a method of detecting lipid processing by a cell. The method involves placing the cell in media containing known physiological concentrations of HDL and LDL and then quantifying the selective uptake of free cholesterol by the cell from the LDL. Comparison of the cholesterol uptake by the test cell with a normal healthy cell of the same type under the same circumstances provides an indication as to the presence or absence of abnormal lipid metabolism by the test cell. Where the test cell deviates significantly from the healthy control, it can be inferred that the test cell shows a defect in lipid metabolism.

Quantification of the cholesterol uptake by the cell from the LDL is accomplished in the same manner as described above in Section II and in Example 1. Suitable cell types include, but are not limited to, virtually any nucleated mammalian cell with human cells being more preferred, and fibroblasts, human vascular smooth muscle cells, human vascular (e.g., aortic) endothelial cells, macrophages, hemapoietic cells, liver, kidney, and human intestinal mucosal cells being most preferred.

VI. Isolating FC Transport Vesicles

As indicated above, the LDL-FC transport mechanism of this invention ultimately internalizes free cholesterol into a cholesterol transport vesicle. Moreover, detection of such cholesterol transport vesicles provides a convenient means of detecting or quantifying LDL-FC transport activity and screening for compounds that up- or down-regulate the LDL-FC transport mechanism of this invention.

Previously isolated cholesterol transport vesicles provide useful positive controls for such assays. For example, addition of isolated cholesterol transport vesicles to a density gradient provides a useful marker to establishing the equilibrium point for a cholesterol transport vesicle in a particular density gradient (a method analogous to the use of peptides of known size to calibrate an electrophoretic gel). Similarly the use of known quantities of isolated transport vesicles provides an effective means for producing standard curves to calibrate a quantitative assay. Other such uses of isolated cholesterol transport vesicles will be known and readily appreciated by one of skill in the art.

Thus, in one embodiment, this invention provides for an isolated cholesterol transport vesicle (CTV). The transport vesicle is one that is endogenously produced by a mammalian, more preferably a human, cell (e.g., a human fibroblast). Moreover, since the vesicle is an intracellular repository for free cholesterol internalized by the LDL-FC pathway of this invention, the vesicle is enriched for free cholesterol such that it has a density ranging from about 1.05 g/ml to about 1.12 g/ml, more preferably from about 1.06 g/ml to about 1.10 g/ml and most preferably from about 1.07 to about 1.09 g/ml.

Although not required, the isolation of free cholesterol transport vesicles is facilitated by the preparation of cells containing high concentrations of such vesicles. When free cholesterol is internalized from labeled low-density lipoprotein in the absence of high-density lipoprotein, free cholesterol rapidly accumulates in the cells. (Typical internalization rates of about 150 ng/min at 37° C. were found at physiological concentrations (about 250 $\mu$g/ml FC). This leads to noticeable enrichment of FC transport vesicles.

The vesicles can be purified from virtually any mammalian cell type with the exception of red blood cells. Particularly preferred cells include, but are not limited to, virtually any nucleated mammalian cell including, but not limited to fibroblasts, human vascular smooth muscle cells, human vascular (e.g., aortic) endothelial cells, macrophages, hemapoietic cells, liver, kidney, and human intestinal mucosal cells.

The vesicles can be purified from cell homogenate made in the absence of detergent and purified by sucrose density gradient centrifugation as described (see, Kaplan & Simoni, *J. Cell. Biol.*, 101: 446–453 (1985) and Lange et al. *J. Biol. Chem.*, 266: 21439–21443 (1991)). In a preferred embodiment a gradient is established between 2% w/v Ficoll in 9% deuterium oxide and 91% "vesicle buffer" (aqueous 140 mM sucrose, 0.5 mM $MgCl_2$, 1 mM EGTA, 2 mM 2-[N-morpholino]ethanesulfonic acid, 70 mM potassium acetate, pH 6.6) and 20% w/v Ficoll in 90% deuterium oxide and 10% vesicle buffer. Each solution contains in addition, a final concentration of 1 mM dithiothreitol. Using such a gradient, cholesterol transport vesicles can be recovered between the densities of about 1.05 g/ml to about 1.12 g/ml, more preferably from about 1.06 g/ml to about 1.10 g/ml and most preferably from about 1.07 to about 1.09 g/ml.

Further purification can optionally be carried out with streptolysin O-covalently linked to activated CNBr-agarose (Pharmacia). This toxin binds directly to FC-rich vesicles and does not react with FC-poor vesicles (Delattre et al., *Cell. Mol. Biol.*, 24: 157–166 (1979)).

One of skill will appreciate that with the density information provided herein and knowledge that the FC-transport vesicles of this invention are enriched for free cholesterol, other isolation methods can be devised with routine experimentation. Such methods include, but are not limited to labeling LDL-FC with a detectable label and then subsequently detecting and isolating vesicles bearing that label, or contacting the cell homogenate fractions with agarose covalently bound to streptolysin O, a composition that specifically binds cholesterol.

In a particularly preferred embodiment, the free cholesterol transport vesicles can be labeled with a detectable label. As indicated above, preferred labels to not significantly alter the density and hence the mobility of the vesicle in a density gradient. Thus, preferred labels are radioactive labels (e.g., $^3H$) as described above.

The detectable label can be incorporated into the cholesterol transport vesicle by any of a number of means well known to those of skill in the art. One approach, for example, can involve chemical conjugation of the label with the cholesterol transport vesicle after isolation of the vesicle.

However, in a preferred embodiment, the label is incorporated into the vesicle by providing the cell with free cholesterol labeled low-density lipoproteins. As the labeled free cholesterol is incorporated into the vesicle, the vesicle itself thereby becomes labeled. Provision of labeled FC LDL and subsequent incorporation of the label into the cholesterol transport vesicles is illustrated in Example 1.

VII. LDL-FC related Kits

This invention provides for kits for the detection and/or measurement of LDL-FC transport pathway activity. Such kits include, but are not limited to, one or more of the following: labeled cholesterol (more preferably LDL containing labeled cholesterol), culture media for the cell, target cells for assaying the activity of agonistic or antagonistic agents, instructions describing the use of the components of the kit for measuring LDL-FC transport pathway activity or for screening for potential agonists or antagonists, cholesterol transport vesicles for use as a positive control, various buffers and reagents for the culture of the cells, the isolation of cholesterol transport vesicles, and the like.

EXAMPLES

The following examples are offered to illustrate, but not to limit the present invention.

Example 1

Identification of an LCL-FC Transport Pathway
Preparation of $^3H$-FC labeled plasma and lipoprotein fractions.

Blood was taken into ice-cooled tubes from normolipemic volunteers who had fasted overnight. Streptokinase (Sigma Chemical Co, St. Louis, Mo., final concentration 150 U/ml) was included as anticoagulant (Miida et al., *Biochemistry*, 29: 10469–10474 (1990)). Plasma was obtained as supernatant following centrifugation (2000× g, 30 min at 0° C.) and used immediately in the studies described below.

To compare the influx of FC from different lipoproteins, native plasma was labeled with 1,2-$^3H$-cholesterol (40–50 Ci/mmol) (New England Nuclear, Boston, Mass., USA). Approximately 0.5–1.0 mCi of isotope was brought to 10–20 μl in ethanol, and injected slowly with stirring into 20–30 ml of plasma at room temperature. The plasma was then incubated at 37° C. for 1–2 h to equilibrate the FC label between lipoprotein fractions.

Dithiobis(2-nitrobenzoic acid) (2 mM) was included to inhibit the in vitro esterification of labeled cholesterol (Fielding & Fielding, Proc. Natl. Acad. Sci. (*USA*) 78, 3911–3914 (1981)). FC equilibration was confirmed from the cholesterol specific activity of each lipoprotein class following fractionation as described below. In other experiments labeling of LDL was carried out following fractionation of native unlabeled plasma on columns (2.5×10 cm) of heparin-agarose (Pharmacia, Piscataway, N.J., USA) which had been previously equilibrated in phosphate-buffered saline (PBS) (pH 7.4). Approximately 6–10 ml of plasma was added at 0–2° C. The nonabsorbed fraction contained HDL and other plasma proteins (Fielding & Fielding, *J. Biol. Chem.*, 261: 5232–5236 (1986)). VLDL and LDL were eluted together with 3M NaCl, 0.01M phosphate (pH 7.4). Individual lipoproteins were isolated from these fractions by ultracentrifugal flotation (Havel et al., *J. Clin. Invest.*, 34: 1345–1353 (1954)). Lipoproteins were dialyzed PBS containing 0.1 mM sodium EDTA (pH 7.4). Immediately before use in individual experiments the medium was brought to 1 mM Ca++, 1 mM $MgCl_2$. If necessary, individual lipoprotein fractions were reconcentrated to their original plasma volume with ultrafiltration membranes (Macrosep: Filtron, Northborough, Mass., USA) at 0° C. Recovery (greater than 95% in these experiments) was assessed by comparing the FC content of the original plasma with the sum of the free cholesterol concentration of the individual fractions recovered.

More than 98% of label in the nonabsorbed fraction in 0.15M NaCl was recovered as HDL between density limits 1.063–1.21 g/ml. More than 95% of label in the fraction (VLDL+LDL) eluted with 3M NaCl was recovered as LDL (1.019<d<1.063 g/ml). The ratio of protein and FC mass in LDL was 2.9±0.1 (Fielding et al., *Proc. Natl. Acad Sci.* (*USA*), 81: 2512–2516 (1984)).

In most experiments, LDL was labeled directly with $^3H$-FC by exchange from albumin-agarose covalent complex essentially as previously described (Miida et al., *Biochemistry*, 29: 10469–10474 (1990)). Briefly, recrystallized human serum albumin (Sigma Chemical Co, St. Louis, Mo., USA) was covalently linked to CNBr-activated Sepharose 6B (Pharmacia). 1,2-$^3H$-FC in ethanol (0.1–1.0 mCi, 10–20 μl/ml gel suspension) was added and the mixture incubated with gentle stirring for 60 mm at 37° C. The labeled suspension was centrifuged (500× g, 1 min) and the gel equilibrated (60 min, 37° C.) with unlabeled LDL prepared as described above. Finally the gel was removed by centrifugation, leaving labeled LDL in the supernatant. LDL total and FC mass was determined fluorimetrically with cholesterol oxidase (Heider & Boyett, *J. Lipid Res.* 19: 514–518 (1978)) in the presence or absence of cholesterol esterase. EC mass was obtained by difference. LDL $^3$H-radioactivity was measured by liquid scintillation spectrometry. FC specific activity in these experiments was $3 \times 10^4$ to $5 \times 10^5$ cpm $\mu g^{-1}$.

In other experiments LDL was labeled with $^{125}$I by the iodine monochloride method (McFarlane, *Nature*, 182: 53 (1958). More than 98% of label was TCA precipitated. Lipid-bound label was <5% when LDL was extracted with CHCl$_3$. The specific activity of $^{125}$I-labeled LDL in these experiments was $2-3 \times 10^5$ cpm $\mu g^{-1}$ protein, equivalent to $6-9 \times 10^5$ cpm of protein label $\mu g^{-1}$ LDL FC.

Cell culture.

Normal skin fibroblasts, two lines of LDL-receptor-deficient fibroblasts (American Type Culture Collection, ATCC GM 0701 and GM 2000) and a receptor internalization-defective line (GM 2408) were cultured in 10% fetal bovine serum in Dulbecco's modified Eagle's medium (DMEM). For individual experiments, cells were cultured in 3.5 cm plastic dishes until nearly confluent. 24 h before use in individual experiments, dishes were transferred into DUEM containing 7–80% of human plasma.

The viability of cells in DMEM containing 7–80% human plasma was compared to cells in PBS or m DMEM-10% fetal bovine serum in terms of the release of label into each medium from cells prelabeled (60 min, 37° C.) with $^{14}$C-adenine (New England Nuclear, 1 $\mu$Ci ml$^{-1}$ medium) (Shirhatti & Krishna, Anal. Biochem., 147: 410–418 (1985)). In each case, $^{14}$C label released into PBS or human serum was the same as or lower than that into the standard growth medium containing 10% fetal calf serum-DMEM (8–10% over 120 min).

Determination of FC influx.

Cell monolayers were washed with PBS (×4) at 37° C. then incubated for 5–120 min with 1 ml of $^3$H-labeled plasma or the same volume of purified labeled lipoprotein in PBS with Ca$^{++}$ and Mg$^{++}$ (complete PBS) on an orbital shaker (1 cycle/sec). The protein concentration of isolated lipoproteins was usually 0.5–1.0 mg ml$^{-1}$. The inclusion of irrelevant protein (purified goat IgG, 4 mg ml$^{-1}$) was without effect on FC flux in these experiments.

Following incubation, each monolayer was washed with human album solution (recrystallized, 4 mg ml$^{-1}$) in complete PBS, then 4× with complete PBS. For lipid analysis or fractionation, the washed monolayers were digested with 1 ml of 0.2N NaOH (24 h, room temperature) before extraction with equal volumes of chloroform and methanol. Portions of chloroform phase were taken for chemical analysis. To determine cell-associated $^3$H-FC label only, cell monolayers were dissolved directly in 4 ml of liquid scintillation cocktail (RPI, Mount Prospect, Ill., USA). Recovery of label under these conditions was greater than 99%. Influx was linear for at least 10 min under these conditions. In some experiments sodium heparin, chloroquine, isobutyl methylxanthine (IBMX) or forskolin (all from Sigma) were included in the influx medium. In other experiments the cells were preincubated with proteinase K (final concentration 10 $\mu$g ml$^{-1}$) in PBS for 8 to 10 min prior to measurement of influx.

The FC and EC mass of cell monolayers was determined before and after incubation with lipoprotein as described above. Portions of the chloroform phase were analyzed for total and free cholesterol. Except where indicated each data point represents the mean of triplicate dishes. The coefficient of variation was <5% of means in these experiments.

Determination of cholesterol efflux.

Fibroblast monolayers were equilibrated with $^3$H-FC-labeled native plasma or with isolated $^3$H-labeled LDL, as specified for each experiment. Following incubation, the dishes were washed with albumin-complete PBS and then (×4) with complete PBS. They were then incubated for 3 min with unlabeled plasma or lipoprotein fractions and the rate of appearance of radioactivity in the medium determined. Samples of medium (100 $\mu$l) were immediately chilled in ice water and centrifuged (10 min, 2000× g) at 0–2° C. $^3$H-cholesterol radioactivity in the supernatant was either assayed directly, or fractionated by agarose gel electrophoresis. FC efflux was linear as previously reported (Kawano et al., *Biochemistry*, 32: 5025–5028 (1993)).

For electrophoresis, 20 $\mu$l portions of labeled medium were added to strips of 0.75% w/v agarose in 0.025M barbital buffer (pH 8.6) and separated as previously described (Fielding et al., *Biochemistry*, 30: 8551–8557 (1991)). 2.5 mm gel fractions were then collected, and radioactivity measured. The location of major lipoprotein classes was determined from strips run simultaneously with whole native plasma equilibrated (60 min, 37° C.) with $^3$H-FC.

Contributions of plasma lipoproteins to cellular cholesterol influx and efflux

Rates of FC influx and efflux between medium and fibroblast monolayers preincubated for 24 h with 7–80% native human plasma in DMEM were determined. Cells equilibrated in 80% compared to 7% v/v plasma contained 35–40% more total cholesterol but only 10–15% more FC. In 50% v/v plasma, cholesteryl ester levels were lower than in 80% plasma but FC levels were almost the same. Rates of transfer of FC between the cells and their extracellular medium were determined for each plasma dilution. Efflux was measured as the rate of transfer of $^3$H-FC radioactivity from labeled native plasma to unlabeled cells. Efflux was determined as the rate of transfer of radioactivity from uniformly labeled cells to unlabeled native plasma medium. As shown in Table 1, both influx and efflux increased almost in parallel by 6-fold when medium

TABLE 1

Effects of medium plasma concentration on rates of cholesterol influx and efflux.

|  | 7% v/v[a] | 50% v/v[a] | 80% v/v[a] |
|---|---|---|---|
| $\mu$g FC dish$^{-1}$ | 13.2 ± 0.2 | 14.8 ± 0.2 | 15.0 ± 0.2 |
| $\mu$g EC dish$^{-1}$ | <0.1 | 1.6 ± 0.6 | 3.0 ± 0.7 |
| FC influx[b] | 27.1 ± 4.6 | 107.0 ± 19.9 | 133.0 ± 20.8 |
| FC efflux[b] | 25.1 ± 0.5 | 102.9 ± 12.8 | 156.6 ± 20.3 |

[a]percent native plasma v/v in DMEM.
[b]Cholesterol influx and efflux are expressed as ng FC transferred min$^{-1}$ between the cell monolayer and 1 ml of plasma medium. Cell monolayers in 3.5 cm dishes were preincubated with unlabeled plasma-DMEM (influx) or with $^3$H-cholesterol labeled plasma-DMEM (efflux) for 24 h. The unlabeled cells were then incubated with $^3$H-FC plasma at the same plasma dilution and cell-associated label determined as described above.The $^3$H-cholesterol labeled cells were incubated at the indicated dilution of unlabeled plasma and efflux determined from medium radioactivity as described above. Each value represents the means ± one SD of six determinations. FC: free cholesterol; EC: esterified cholesterol.

FC content was increased 11-fold. Maximal rates of influx and efflux reached as much as 1% of cell FC min-1. These data show that there is a rapid bidirectional transfer of FC between the cell monolayers and medium-lipoproteins, whose rate is strongly dependent on medium FC concentration.

Cellular FC efflux to plasma media is mainly mediated by HDL (Francone et al., *J. Lipid Res.*, 31: 2195–2200 (1990)). The prebeta-migrating fraction of small HDL appears to be particularly active in this pathway (Castro & Fielding, *Biochemistry*, 27: 25–29 (1988); Huang et al., *Arterioscler. Thromb.*, 13: 445–458 (1993)). The contributions of HDL and LDL to FC influx were determined, and compared to that catalyzed by unfractionated native plasma (Table 2). Each lipoprotein was tested at its original plasma concentration. As shown in Table 2, the greatest influx was obtained from LDL (about 85% of the rate with native plasma). This value exceeded the

TABLE 2

Contributions of LDL and HDL to influx from native plasma.

|  | Native Plasma | | LDL | | HDL | |
| --- | --- | --- | --- | --- | --- | --- |
|  | FC[a] | Influx[b] | FC[a] | Influx[b] | FC[a] | Influx[b] |
| Experiment 1 | 409 | 79.0 | 282 | 58.9 | 102 | 14.6 |
| Experiment 2 | 367 | 63.6 | 231 | 55.9 | 118 | 15.0 |
| Experiment 3 | 432 | 58.0 | 284 | 51.5 | 149 | 11.5 |
| Means | 403 ± 33 | 69 ± 11 | 266 ± 30 | 56 ± 4 | 123 ± 24 | 14 ± 2 |

[a]FC concentration of plasma and plasma fractions was determined enzymatically and is expressed as $\mu$g FC ml$^{-1}$ original plasma volume.
[b]Rate of $^3$H-cholesterol influx is expressed as ng min$^{-1}$ following determination of cell-associated $^3$H-cholesterol radioactivity over 5 min. Influx was linear over this time course.

proportion of total FC in plasma associated with LDL. While HDL contributed on average 35% of plasma FC, the rate of FC influx when only HDL was present represented only about 15% that determined with native plasma. The sum of influx catalyzed by HDL and LDL was similar to that measured with native plasma. These data indicated that most FC entering the cells from media containing native plasma originated from LDL.

To determine whether cellular factors contributed to the increased influx of LDL FC with increasing LDL concentration, cells were equilibrated with unlabeled 7% v/v plasma in DMEM and then transferred to unlabeled 80% v/v plasma medium. At zero time and at intervals thereafter up to 24 h in the 80% medium, triplicate dishes of cells were washed, and $^3$H-FC labeled LDL (94 $\mu$g FC ml$^{-1}$) added for 10 min at 37° C. to determine the rate of influx of FC. The initial rate of influx into 7% plasma-DMEM medium was 39.8±7.0 ng min$^{-1}$. This rate was almost unchanged at the end of 24 h m 80% plasma-DUEM medium (49.4±8.3 ng min$^{-1}$) (difference not significant). This result indicates that the increase in cholesterol influx as a function of medium plasma FC content shown in Table 1 was solely a function of medium LDL concentration over the 7–80% plasma range.

The concentration dependence of influx from $^3$H-FC labeled LDL is shown in FIG. 1. The data illustrate a saturable pathway with a maximum velocity of 80–100 ng$^{-1}$ (3 experiments) and a Km$_{app}$ of 250±20 $\mu$g LDL-FC ml$^{-1}$, equivalent to 0.8 mg ml$^{-1}$ LDL protein (Fielding et al., *Proc. Natl. Acad Sci.* (USA) 81: 2512–2516 (1984)).

Figure 2:
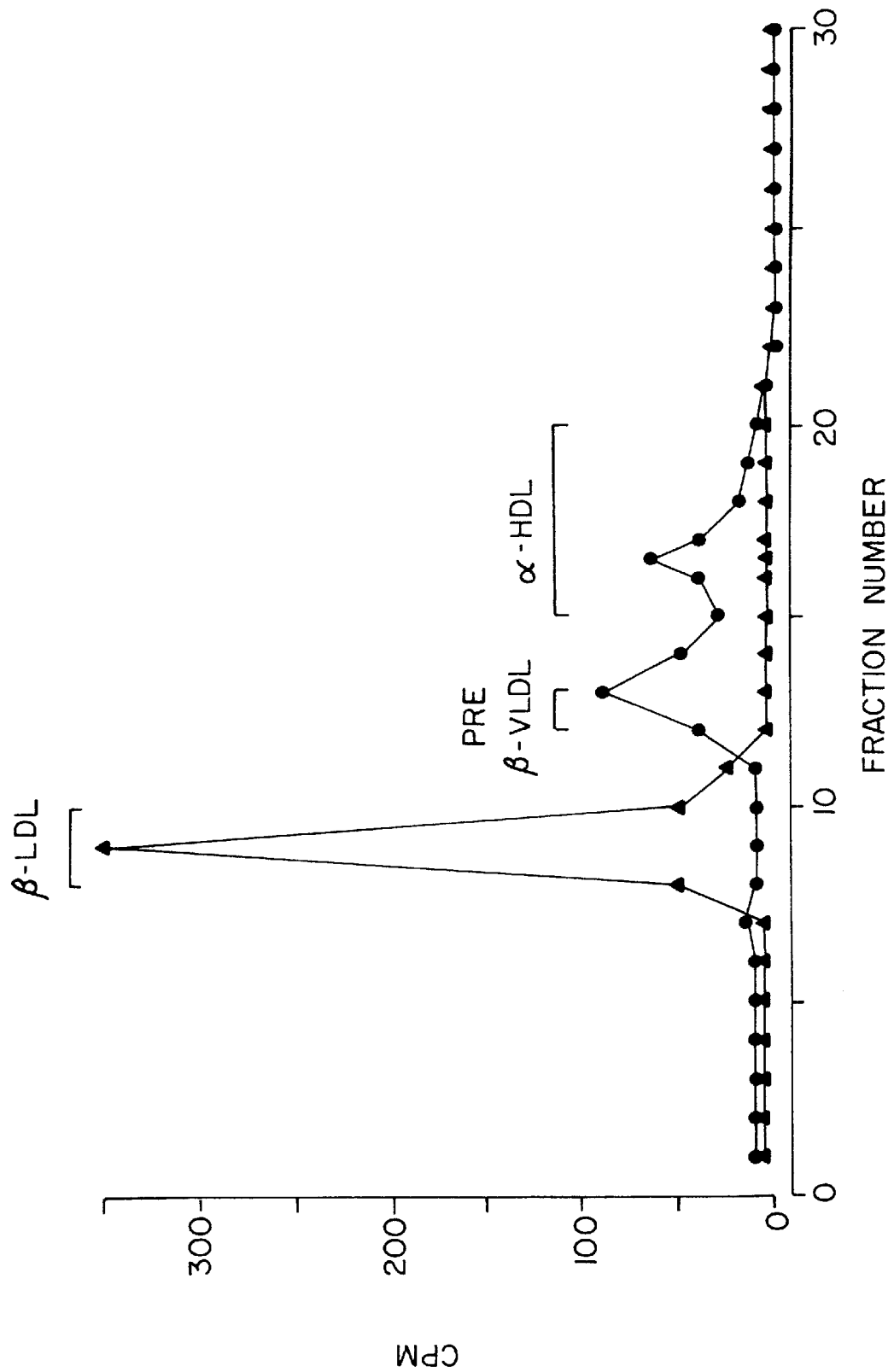
FIG. 2 shows the efflux of radioactivity from cells prelabeled with $^3$H-FC labeled LDL. Unlabeled cells equilibrated in 7% plasma-DMEM were washed, incubated with labeled LDL (10 min, 37° C.) then washed with PBS-albumin and PBS as described in the legend to FIG. 1. Unlabeled native plasma was then added for 1 min at 37° C., then a sample (20 μl) taken for immediate agarose gel electrophoresis. 2.5 mm wide gel strips were collected after separation and analyzed for contained radioactivity. Closed circles, label recovered from plasma incubated with the cell monolayer. Closed triangles, original $^3$H-FC labeled LDL run in a separate agarose strip. The positions of major lipoprotein species were determined from a sample of whole plasma prelabeled with $^3$H-FC and electrophoresed simultaneously. FC efflux was 17.8 ng min$^{-1}$ in this experiment. Label recovered in total HDL was >90% of that applied.

Cells were incubated (10 min) with $^3$H-FC-labeled LDL. These were then transferred for 3 min to unlabeled native plasma. Samples of this plasma were then fractionated by agarose-gel electrophoresis (FIG. 2). Almost the whole of radioactivity was recovered in those fractions which co-migrated with prebeta- and alpha-HDL, consistent with earlier findings (Fielding et al., *Biochemistry*, 30: 8551–8557 (1991); Miida et al. *Biochemistry*, 29: 10469–10474 (1991)). None was detected co-migrating with the LDL or albumin fractions of plasma. These data indicated that transfers of FC occurring at the cell surface were represented for the most part by the uptake of FC from LDL into the cell, and the release of cellular FC to HDL in the medium.

Receptor-mediated endocytosis and free cholesterol transfer

The rate of delivery of FC by the endocytosis of intact LDL was determined from the rate of appearance of TCA-soluble $^{125}$I-radioactivity from $^{125}$I-labeled LDL. The rates of influx of $^3$H-FC label from LDL to normal fibroblasts and to several lines of LDL receptor-deficient cells were also compared under the same conditions and assayed as described above.

The appearance of TCA-soluble label from $^{125}$I-LDL was measured over 3 h at 37° C. Its rate was linear and its magnitude (1.2±0.3 ng LDL protein min$^{-1}$; 3 experiments) represents an LDL FC transfer to the cells of 0.4±0.1 ng LDL free cholesterol min$^{-1}$ from the FC/protein mass ratio of LDL determined experimentally. Under the same conditions the rate of selective transfer of $^3$H-FC label from LDL was 32.4±3.5 ng min$^{-1}$, about 80-fold greater.

The rate of FC transfer from $^3$H-FC labeled LDL to normal, receptor-deficient and internalization-deficient fibroblast monolayers was compared. In a representative experiment at an LDL FC concentration of 46 $\mu$g ml$^{-1}$, the rate of transfer to nominal cells was 15±3 ng min$^{-1}$; while the rate of influx from the same preparation to receptor-deficient cells was 16±3, 15±3 and 19±3 ng min$^{-1}$ respectively for GM 2000, GM 0701 and GM 2408 lines.

These data suggest that the influx of LDL FC to cell monolayers maintained in the presence of human plasma was largely independent of the receptor-mediated endocytosis of intact LDL.

Cellular effects of LDL-mediated FC influx.

Figure 3:
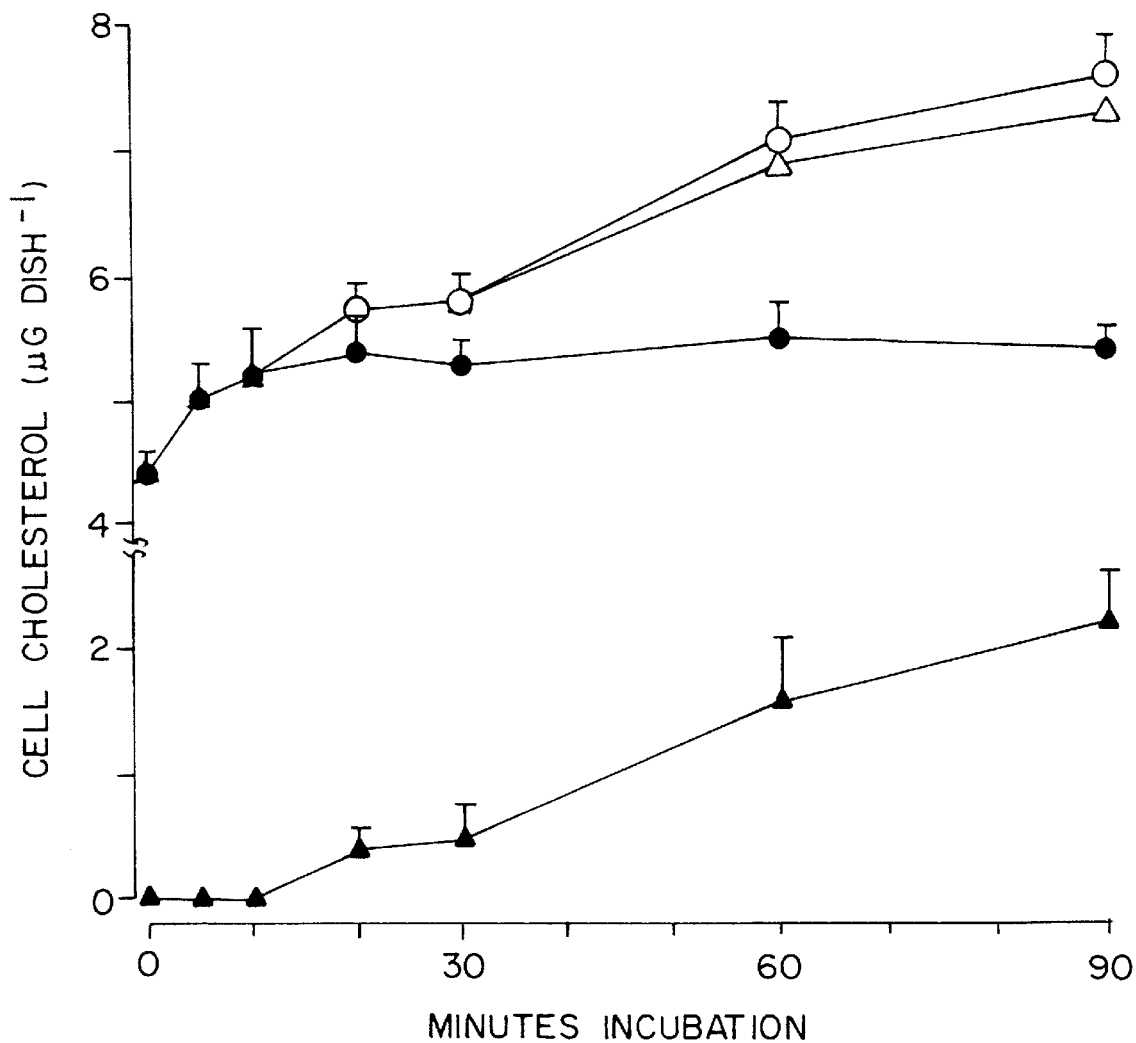
FIG. 3 shows cell free and ester cholesterol mass and cholesterol radioactivity as a function of time in unlabeled cells incubated with $^3$H-FC labeled LDL. Closed circles, cellular FC mass determined enzymatically; open circles, total cholesterol mass; closed triangles, EC mass determined as the difference between total and free values; open triangles, predicted total cholesterol mass based on the sum of the measured initial content of the cells (4.4±0.2 μg dish$^{-1}$) together with cell-associated $^3$H-cholesterol from labeled LDL based on a measured specific radioactivity of 5.8×10$^4$ cpm μg$^{-1}$. Data points are the means of six measurements in each case.

$^3$H-FC-labeled LDL was incubated with fibroblast monolayers at 37° C. for up to 90 min. At intervals, cells were washed, and assayed for FC and EC mass and radioactivity. Before the addition of LDL, the cells contained no detectable EC (FIG. 3). Transfer to LDL solution was associated with an increase in cellular FC mass without the appearance of EC over the first 10 min of incubation. Beyond this point, as cell-associated cholesterol label continued to increase, FC mass remained almost constant while EC mass began to accumulate.

Cell-associated cholesterol radioactivity and the increase in cell total cholesterol mass were compared. As shown in FIG. 3, when the specific activity of LDL was used to convert the increase in cell-associated label to mass, calculated values for cellular cholesterol mass were similar to those determined directly, indicating that in the absence of other lipoproteins almost the whole of FC taken up from labeled LDL was retained within the cells. Since much of this cholesterol was esterified, this finding shows that at least some of the FC internalized from $^3$H-FC-labeled LDL must be accessible to microsomal acyl CoA:cholesterol acyltransferase (ACAT), the only significant source of EC in these cells (Suckling & Stange, *J. Lipid Res.*, 26: 647–671 (1985)). This was confirmed by determining the specific activities of FC and EC in extracts of cells incubated with LDL for 60 and 90 min. These did not differ significantly, confirming that internalized LDL FC was available for esterification and in equilibrium with cellular EC.

Kinetics of cellular FC influx mediated by LDL

The mechanism of LDL-mediated influx of labeled FC was studied further by measuring the ability of unlabeled lipoprotein fractions to displace cell-associated label, as a function of the time during which the influx of $^3$H-FC took place.

Figure 4:
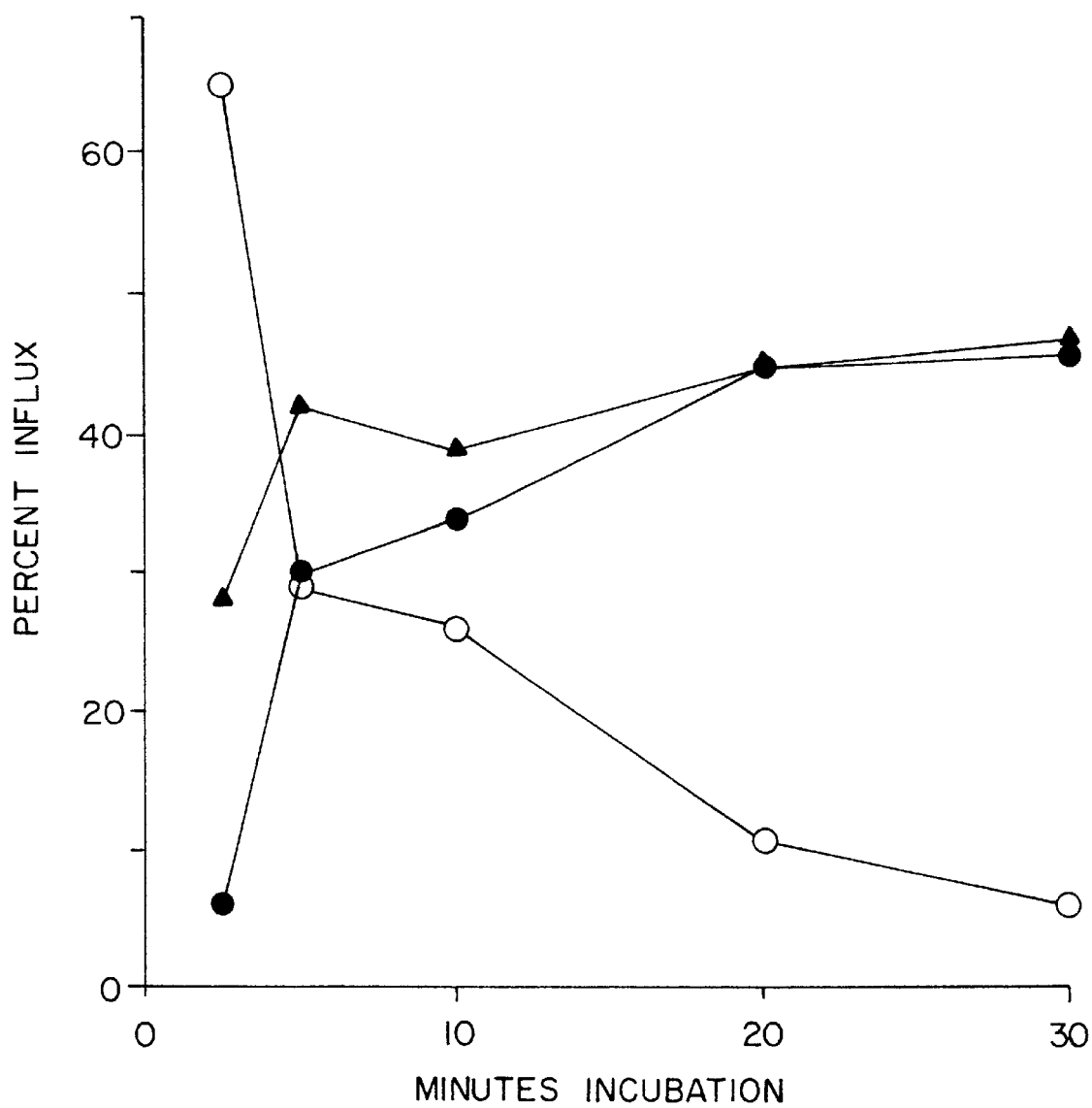
FIG. 4 shows the distribution of cell-associated $^3$H-FC from LDL as a function of time. Label released by unlabeled LDL (open circles); label released by unlabeled HDL but not unlabeled LDL (closed triangles) and label released with neither LDL or HDL (closed circles) expressed as percent of total label released. LDL specific activity was 3.1×10$^4$ μg ml$^{-1}$. All fractions are defined in terms of label released by either unlabeled lipoprotein within 5 min of incubation at 37° C.

Cell monolayers equilibrated with 7% plasma-DMEM were first incubated with $^3$H-FC labeled LDL as described above. At intervals, dishes of cells were washed, then incubated with unlabeled LDL or HDL at their plasma concentrations. A fraction of cell-associated label was rapidly released; maximum recovery in the medium occurred within 10 min at 37° C. In FIG. 4, the proportions of cell label which were LDL-releasable, LDL-resistant but HDL-releasable, and resistant to both LDL and HDL are shown as a function of time.

The major part of cell-associated LDL $^3$H-FC could initially be dissociated into the medium with cold LDL; but this proportion decreased with time as label accumulated in the cells. The proportion of label resistant to LDL but released by HDL was initially low but reached 40–60% (3 experiments) after 15 min. Label inaccessible to either LDL or HDL over the time course of these experiments was 30–50% of total label after 15 min of incubation at 37° C. These data are consistent with a mechanism in which LDL 3 H-FC was first bound to the cell surface, and then transferred to a compartment from which it was either released by HDL to the medium, or transferred into the cell for further metabolism.

Figure 5:
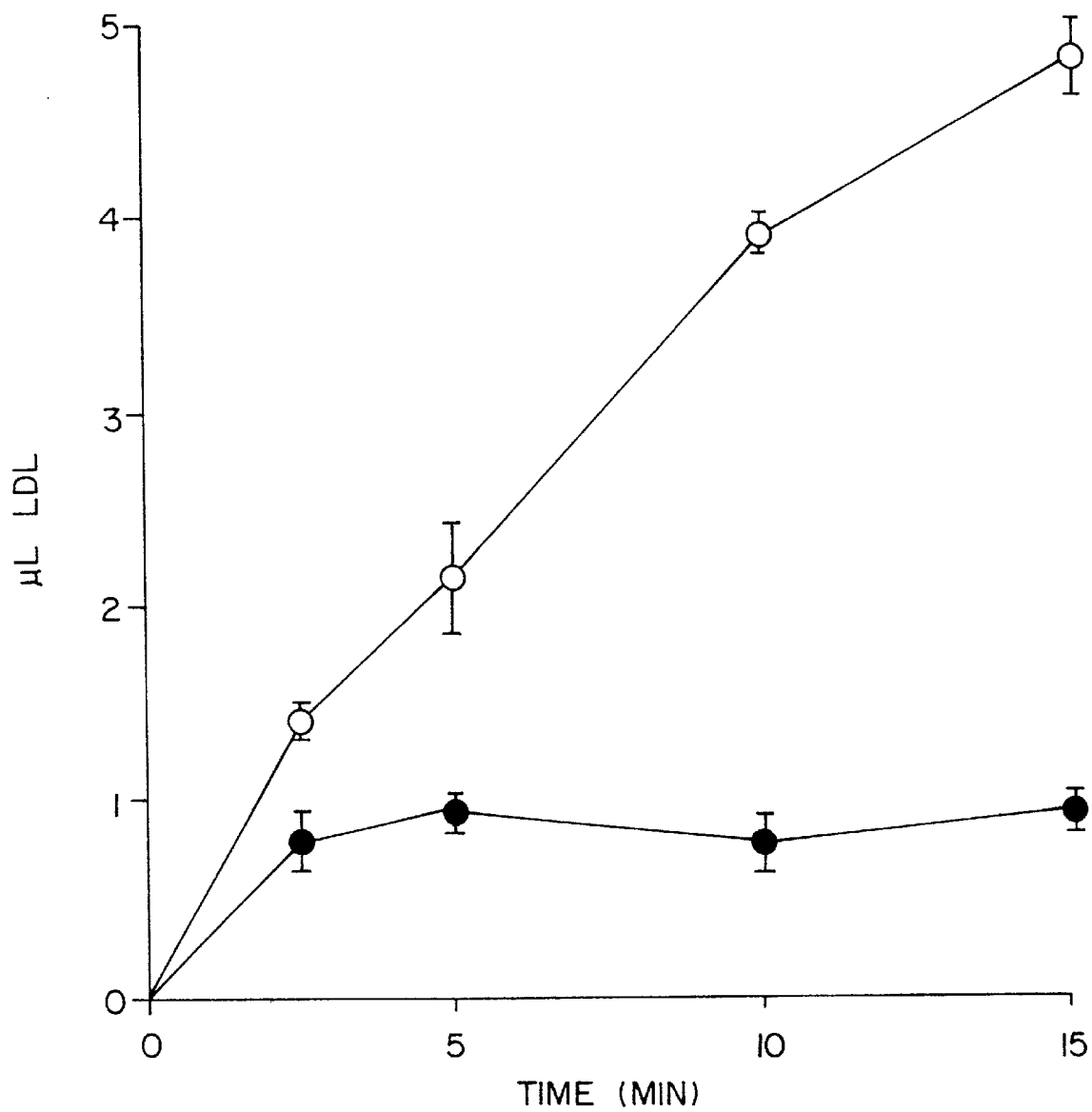
FIG. 5 illustrates the association of LDL $^{125}$I-protein and $^3$H-FC labels with fibroblast monolayers as a function of time. LDL (69 μg FC ml$^{-1}$) was labeled with either isotope as described in Example 1 and incubated with unlabeled cell monolayers for the period shown. After washing with PBS-albumin and PBS, cell-associated label was determined following solubilization of the cell monolayers with 0.2N NaOH. Data are expressed in terms of the volume of LDL solution associated with the cells at each time point to allow direct comparison with the cell association of both labels. Values shown are the means of three different experiments. Open circles, LDL $^3$H-free cholesterol; closed circles, LDL $^{125}$I-protein.

Further information on the mechanism of FC influx was obtained by comparing the cell association of LDL labeled in the protein moiety with 125I, or in the free cholesterol moiety with $^3$H-FC. Unlabeled cell monolayers were incubated with the same concentration of either $^3$H- or $^{125}$I-labeled LDL for 2.5–15 min at 37° C. At each time point the dishes were washed and bound 125I-protein or $^3$H-FC radioactivity determined. As shown in FIG. 5, cell-associated $^{125}$I-label reached a maximum with 2.5 min of incubation that was maintained during a 15 min incubation period. In contrast, $^3$H-FC label increased nearly linearly over the same period. To allow comparison of protein and free cholesterol labels, the data have been expressed as the uptake of LDL medium volume min$^{-1}$. In these units the uptake of LDL FC by the cells represented 0.3–0.4 µl LDL solution min$^{-1}$, equivalent to 20.7 ng FC min$^{-1}$. In four experiments with different LDL preparations the final ratio of $^3$H/$^{125}$I label was 5.6±1.5 following 15 min of incubation.

Figure 6:
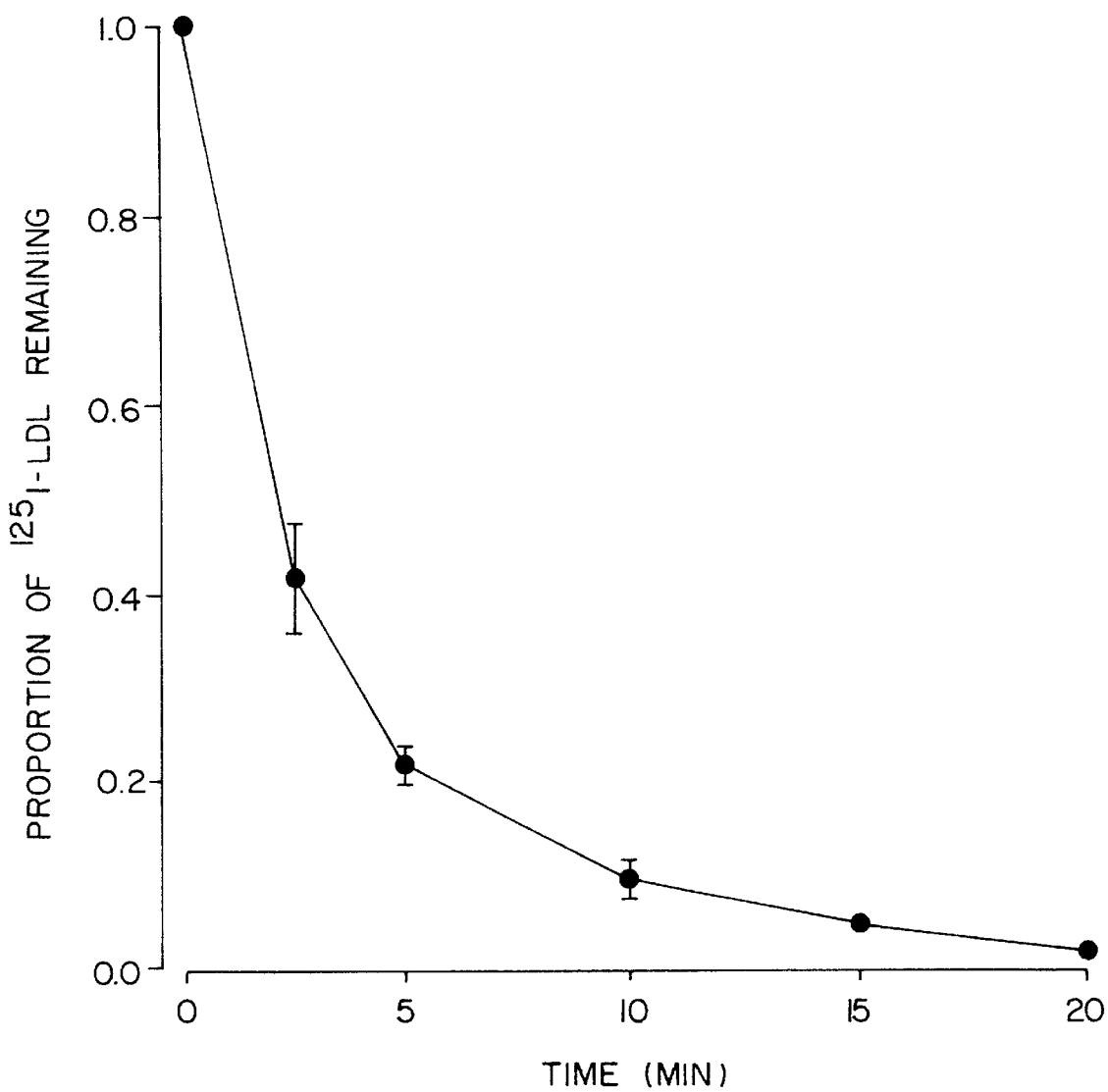
FIG. 6 illustrates the turnover of $^{125}$I-labeled LDL at the cell surface after addition of unlabeled LDL. Labeled LDL (70 μg FC ml$^{-1}$) was incubated with fibroblast monolayers for 10 min at 37° C. The cells were then washed, and incubated for the time shown with unlabeled LDL at the same concentration. Remaining cell associated label was determined as a function of time with unlabeled LDL following extraction of the cells with 0.2N NaOH. Data from three independent experiments is expressed relative to initial cell content of $^{125}$I-radioactivity.

In other experiments, 125I-labeled LDL was incubated (10 min) with unlabeled cell monolayers. These were then washed and transferred to medium containing unlabeled LDL at the same concentration. The whole of bound $^{125}$I-label was rapidly displaced (FIG. 6) with a half-time of 1.5±0.5 mm (3 experiments).

The data in FIG. 5 suggest that LDL first bound to the cell, then transferred part of its FC content to the cell surface before being displaced by new particles. The data shown in FIG. 6 indicate that little if any bound LDL was retained at the cell surface.

Inhibition of the uptake of LDL-derived free cholesterol

Figure 7:
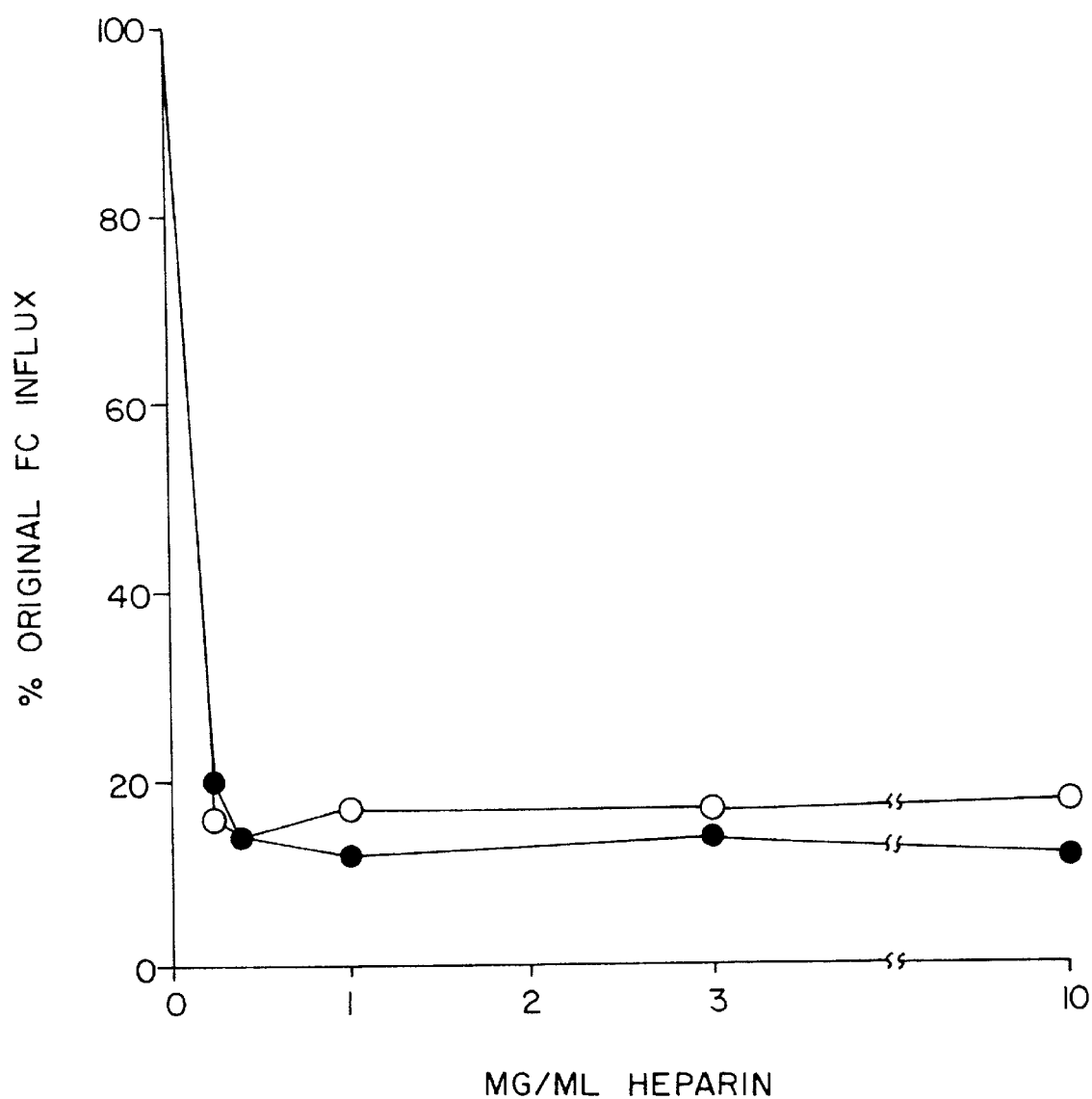
FIG. 7 illustrates the inhibition of LDL $^3$H-FC influx by sodium heparin. Monolayers of either normal fibroblasts (closed circles) or LDL-receptor deficient cells (GM 2000 line, open circles) were incubated with LDL (150 μg FC ml$^{-1}$) for 10 min at 37° C. in the presence of the indicated concentration of heparin. The plates were then washed as described in the legend to FIG. 1 and extracted to determine cell-associated radioactivity. Data are expressed as a percent of the label bound in the absence of heparin.

As shown in FIG. 7, the influx of FC from LDL was similarly inhibited by heparin in both normal and LDL-receptor deficient (GM 2000) cells. Approximately 80% inhibition was obtained at 0.1 mg/ml heparin. In contrast to LDL receptor-mediated influx (Goldstein & Brown, 1974) or HDL-mediated efflux (Kawano et al., *Biochemistry*, 32: 5025–5028 (1993)) the uptake of $^3$H-FC LDL label was only slightly inhibited (7±6%; 4 experiments) when the cell monolayers was pretreated with proteinase K under the same conditions as previously.

HDL mediated efflux has been reported dependent upon cellular cAMP levels and activity of signaling intermediates, (Oram et al., *Arterioscler. Thromb.*, 11: 403–414 (1991); Hokland et al., *J. Biol. Chem.*, 268: 25343–25349 (1993); Voyno-Yasentskaya et al., *Proc. Natl. Acad Sci.* (USA), 90: 4256–4260 (1993)). The effect of these agents on the internalization and retention of LDL-derived FC was determined. As shown in Table 3, there was no effect on LDL FC uptake by forskolin or isobutyl methylxanthine under conditions shown previously to modify HDL-mediated signaling (Oram et al., *Arterioscler. Thromb.*, 11: 403–414 (1991)). Azide and vanadate, effective inhibitors of ATPases catalyzing transmembrane ion transport (Pederson & Carafoli, *Trends Biochem. Sci.*, 12: 146–150 (1987)) were also without effect on LDL FC transfer. There was no effect of progesterone, even at a concentration (30 µM) which would maximally inhibit fibroblast ACAT activity (Goldstein et al., *Proc. Natl. Acad. Sci.* (USA), 75: 1877–1881 (1978)) or cholesterol transport in hepatocytes (Lange, *J. Biol. Chem.*, 269: 3411–3414 (1994)). However N-ethylmaleimide (NEM) and KNO$_3$, inhibitors of the ATPases required for vesicular transport between cell compartments (Pederson & Carafoli, *Trends Biochem. Sci.*, 12: 146–150 (1987); Tageya et al., *J. Biol. Chem.*, 268: 2662–2666 (1993)) both strongly (>75%) inhibited the uptake of LDL FC by these cells.

TABLE 3

Effects of metabolic inhibitors on the uptake of $^3$H-cholesterol from LDL.

|  | Concn | FC Influx (µg)$^a$ | % |
|---|---|---|---|
| PBS only | — | 1.31 ± 0.05 | 100.0 |
| Na-azide | 1 mM | 1.18 ± 0.02 | 89.5 |
| NH$_4$-vanadate | 1 mM | 1.36 ± 0.08 | 103.2 |
| N-ethylmaleimide | 2 mM | 0.40 ± 0.01 | 30.0 |
| KNO$_3$ | 50 mM | 0.28 ± 0.02 | 21.0 |
| Progesterone | 30 µM | 1.28 ± 0.06 | 97.3 |
| Forskolin | 30 µM | 1.39 ± 0.01 | 105.3 |
| IBMX | 100 µM | 1.46 ± 0.04 | 110.8 |
| Chloroquine | 20 µM | 1.34 ± 0.04 | 102.3 |

Confluent cell monolayers were cultured in unlabeled 7% plasma-DMEM, washed in PBS (x4), pre-equilibrated in PBS (30 min, 37° C.) with the factors shown at the indicated concentration (or with PBS only, in the control dishes) then incubated (60 min, 37° C.) in $^3$H-cholesterol labeled LDL-FC (60.2 µg ml$^{-1}$). Cells were then washed and extracted as described above. Values shown are means ± one SD for triplicate dishes.
$^a$Influx is calculated from cell-associated $^3$H-label (LDL-FC specific activity 2.24 × 10$^4$ cpm µg$^{-1}$).

With cells prelabeled to equilibrium (24 h) with $^3$H-FC, inhibition by NEM was complete within 30 min. of the extracellular addition of inhibitor. Maximal inhibition was obtained at 2–5 mM NEM in intact cells, compared to 1 mM in assays of vesicular transport in vitro (Tageya et al., *J. Biol. Chem.*, 268: 2662–2666 (1993)).

Figure 8:
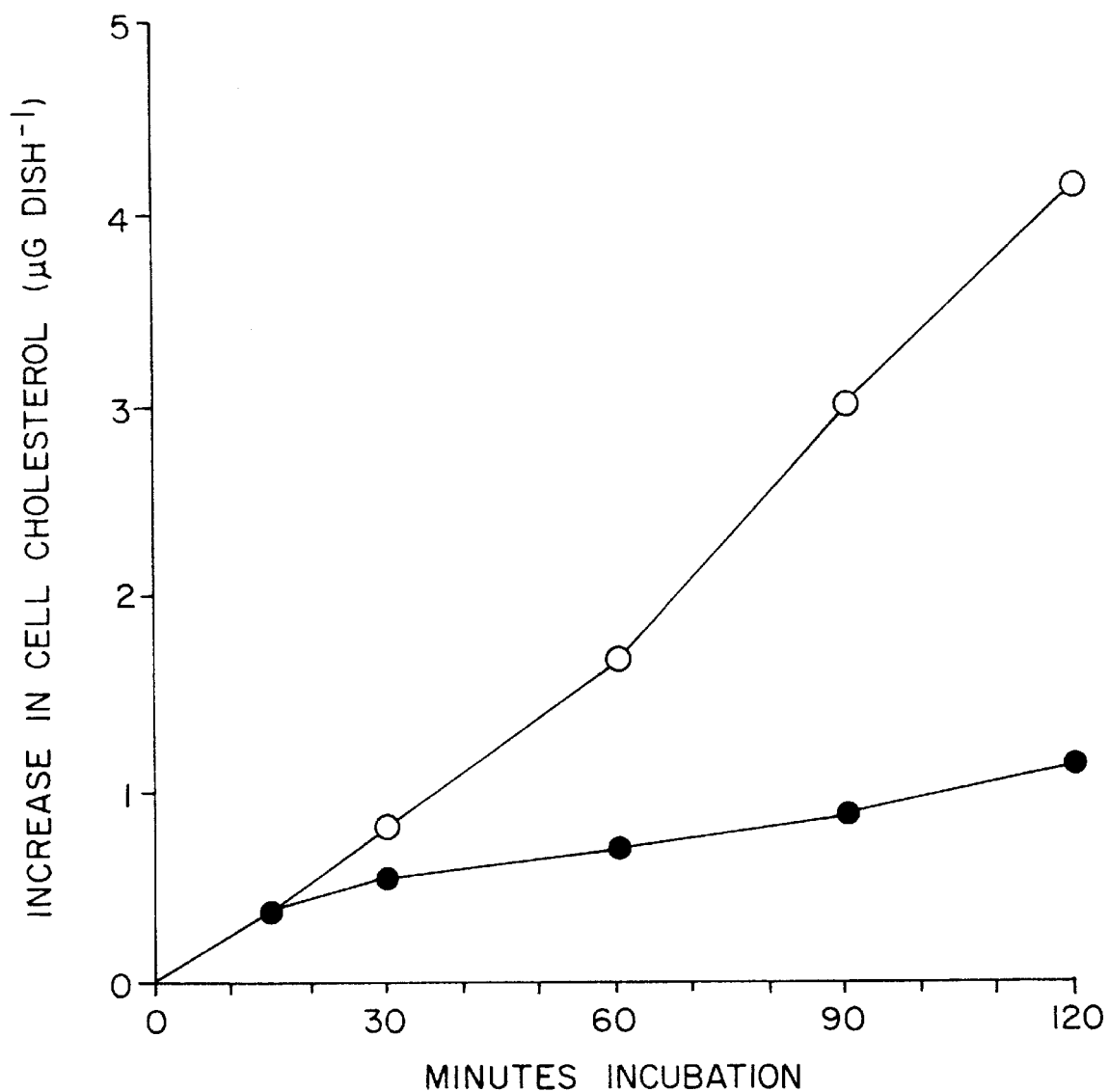
FIG. 8 shows the time course of uptake of $^3$H-FC labeled LDL in the presence or absence of 5 mM NEM. Cells in 7% plasma-DMEM were washed, preincubated (30 min, 37° C.) with PBS or PBS-NEM, then transferred $^3$H-FC LDL solution (91 μg FC ml$^{-1}$) for the indicated period. Open circles, without NEM; closed circles, with NEM. Data points represent means of triplicate dishes.

The time course of inhibition of $^3$H-FC transfer from labeled LDL to unlabeled fibroblast monolayers preincubated (30 min ) with NEM is shown FIG. 8. For the first 10–15 min of incubation with LDL, there was no effect of NEM on the cellular uptake of LDL FC. Upon further incubation an almost complete (>80%) inhibition of the uptake of $^3$H-FC from LDL. This was associated with a parallel inhibition of accumulation of cholesterol mass (Table 4). A comparable time course to that shown in FIG. 8 was obtained for cells preincubated with 50 mM KNO$_3$ (data not shown).

TABLE 4

Effects of N-ethylmaleimide (NEM) on cholesterol transfer between cell monolayers and plasma lipoproteins:

|  | Control | +NEM |
|---|---|---|
| Δ total cholesterol (μg dish$^{-1}$)[a] | 4.1 ± 0.3 | 0.4 ± 0.2 |
| Lipoprotein-resistant label[b] | 0.57 ± 0.03 | 0.24 ± 0.03 |
| % efflux to plasma (3 min)[c] | 13.3 ± 0.1 | 32.4 ± 0.2 |

Values represent data obtained in cells incubated in the presence or absence of 2 mM NEM.
[a]Increase in cellular cholesterol mass determined enzymatically over 120 min. at 37° C. Initial cell FC was 5.0 ± 0.2 μg.
[b]Proportion of cell cholesterol label retained in the cells following incubation (10 min, 37° C.) with 80% v/v plasma-PBS;
[c]Percent loss of label from cells prelabeled (10 min, 37° C.) with $^3$H-cholesterol labeled LDL, during incubation (3 min, 37° C.) with unlabeled 80% v/v plasma-PBS.

Further information on the mechanism of NEM-mediated inhibition was obtained by preincubating NEM-blocked or unblocked cells with $^3$H-FC labeled LDL for 10 min, before the inhibition of $^3$H-FC transfer was detectable (FIG. 8). The initial rate of appearance of cellular $^3$H-FC in the medium, and the proportion of label resistant to lipoprotein-mediated efflux, were then compared in NEM-blocked and unblocked control cells. As shown in Table 4, NEM mediated an increased rate of efflux, and reduced the proportion of cellular label transferred to the lipoprotein-resistant compartment.

Example 2

Intracellular Transport of Low Density Lipoprotein-derived Free Cholesterol Begins at Clathrin-coated Pits and Terminates at Cell Surface Caveolae Preparation of $^3$H-FC-labeled LDL Plasma was obtained from the blood of normal donors who had fasted overnight. LDL was isolated from plasma by affinity chromatography on heparin-agarose (Pharmacia-LKB, Piscataway, N.J., USA) as described above. LDL-FC was labeled to a final specific activity of 2–6×10$^4$ cpm μg$^{-1}$ by incubation (60 min, 37° C.) with agarose-human serum albumin covalent complex labeled with 1,2-[$^3$H]-FC (45–56 Ci mmol$^{-1}$; NEN, Boston, Mass.) (Miida et al. (1990) Biochem., 29: 10469–10474). Free cholesterol (FC) mass was measured fluorimetrically with cholesterol oxidase (Helder & Boyett (1978) J. Lipid Res. 19: 514–518). Phospholipid mass was measured colorimetrically as inorganic phosphate (Emmelot et al., (1964) Biochim. Biophys. Acta 90: 126–145).

Cell Culture

Normal and LDL receptor-deficient fibroblasts (GM 2000 line, American Type Culture Collection, Rockville, Md.) were grown to near confluence in plastic dishes in Dulbecco's modified Eagle's medium (DMEM) containing 10% fetal calf serum. The cells were transferred to media containing human plasma or LDL for individual experiments described below.

Uptake of FC from LDL

To measure the rate of selective internalization of $^3$HFC from LDL cell monolayers were washed with Dulbecco's phosphate-buffered saline pH 7.4 (PBS) (CaCl$_2$, 0.1 gl$^{-1}$; KCl and KH$_2$PO$_4$ both 0.2 gl$^{-1}$; NaCl 8 gl$^{-1}$, Na$_2$HPO$_4$ 1.15 gl$^{-1}$; NaH$_2$PO$_4$ 7H$_2$O). and then incubated at the temperature indicated for 1–15 min with $^3$H-FC labeled LDL (50–200 μg ml$^{-1}$ FC). Unbound labeled LDL was removed by washing with PBS, and adsorbed intact $^3$H-LDL was then displaced with excess unlabeled LDL (60 min, 0–2° C.). The dishes were washed with PBS-recrystallized human serum albumin (5 mg ml$^{-1}$) and four times with PBS alone. The cells were solubilized with liquid scintillation cocktail (3a70b, RPI, Mount Prospect, Fla., USA) and radioactivity measured by liquid scintillation spectrometry.

In some experiments, the cells were preincubated (60 min) with metabolic inhibitors affecting different steps of intracellular transport. $^3$H-FC labeled LDL was then added, together with inhibitor. The experiment was then completed as described above.

Cytochalasin D, monensin, brefeldin A, nocozadole, taxol and vinblastine were purchased from CalBiochem, San Diego, Calif. Trifluoperazine and N-ethyl maleimide were purchased from Sigma Chemical Co, St Louis, Mo., USA. Bafilomycin Al was obtained from Wako Chemical, Richmond, Va., USA. These reagents were dissolved as a stock solution in dimethyl sulfoxide (DMSO) prior to dilution (>500-fold) in PBS or DME-0.01M Hepes buffer (pH 7.4). There was no effect of carrier alone on the uptake of $^3$H-FC label by the cells.

Transfer of FC between intracellular compartments.

Early endosomal vesicles were labeled with LDL-derived $^3$H-FC by a modification of procedures described by Woodman & Warren (1991) J. Cell Biol., 112:1133–1141. Fibroblast monolayers in 10 cm dishes were washed in ice-cold PBS. The cells were labeled by incubation (2 h, 4° C.) with $^3$H-FC LDL. The monolayers were washed in PBS and brought to 31° C. for 0–15 min. The cells were then quickly chilled on ice, and cold unlabeled LDL was added (15 min, 4° C.) to displace any remaining surface-bound labeled LDL and all subsequent steps were carried out at 0–4° C.

Cells from three 10 cm dishes were used for each gradient. Monolayers were washed with 140 mM sucrose, 0.5 mM MgCl$_2$, 1 mM EGTA, 20 mM 2-[N-morpholino] ethanesulfonic acid (MES), 70 mM potassium acetate, pH 6.6 ('vesicle buffer') (Woodman & Warren, supra.). The cells were scraped from the dishes. Dithiothreitol (1 mm) and protease inhibitors (PMSF, 200 μg ml$^{-1}$; benzamidine 0.5 mM; soybean trypsin inhibitor 10 μg ml$^{-1}$; leupeptin 1 μg ml$^{-1}$) were added. The cells were broken with a Dounce homogenizer (15 strokes) and the homogenate centrifuged at 500× g for 5 min. Ribonuclease A (50 μg ml$^{-1}$) was added. After 30 min a second centrifugation was carried out (7000× g, 30 min). Supernatant (~2 ml) was layered on a 10 ml continuous gradient of 2% Ficoll-9% D$_2$O to 20% Ficoll-90% D$_2$O in vesicle buffer containing 1 mM dithiothreitol. Centrifugation in a Beckman SW41 rotor was carried out at 80,000× g for 16 h. Fractions (~0.6 ml) were collected dropwise and the distribution of FC label determined. Because of slight variation in fraction size between gradients, data were normalized to 20 fractions for comparison between experiments. Solution density was determined gravimetrically using 100 μl portions of each fraction. The density of a given fraction was reproducible ±0.5% between experiments.

The identity of intracellular transport intermediates and the extent of any crosscontamination between fractions was established using specific antibodies to protein markers, labeled ligands of receptor proteins, and assays of enzyme proteins. Antibodies included monoclonal antibody to human clathrin heavy chain (ICN Pharmaceuticals, Costa Mesa, Calif., USA), anti-human caveolin polyclonal antibody (Transduction Laboratories, Lexington, Ky., USA) and anti-mannose-6-phosphate receptor protein. For antibody assays, portions of gradient fractions were mixed with 0.1 ml of recrystallized human serum albumin (2 mg ml$^{-1}$ in PBS) and brought to 1 ml with PBS. Protein was precipitated with trichloroacetic acid (final concentration 10% w/v). Following centrifugation (5000× g, 15 min) the pellets were washed with 70% aqueous ethanol, and dissolved in 20 μl of SDS gel sample buffer. After 12% SDS-polyacrylamide electrophoresis, proteins were transferred to nitrocellulose (0.2 μm pore size, S & S, Keene, N.H., USA). Following incubation with individual primary antibodies, blots were incubated with second antibody (anti- mouse or rabbit IgG, Transduction Laboratories, Lexington, Ky., USA) conjugated with horse radish peroxidase, and then visualized with Super-Signal CL-HRP substrate (Pierce, Rockford, Ill., USA). The distribution of antigen between different gradient fractions was determined with a computerized scanner (ImageQuant, Molecular Devices, Sunnyvale, Calif., USA).

Human transferrin (Sigma Chemical Co., St. Louis, Mo., USA) was $^{125}$I-labeled with chloramine T (Markwell (1982) *Anal. Biochem.*, 125: 427–432). Labeled protein was incubated with the cell monolayers, lysate was prepared, and density gradient fractionation was carried out, as described for labeled LDL, except that unincorporated cell-surface transferrin was removed with desferroxamine (Woodman & Warren, supra.) rather than cold LDL.

Enzyme assays were carried out directly on samples of gradient fractions. Alkaline phosphatase was assayed by spectrophotometry at 420 nm after incubation with p-nitrophenyl phosphate (CalBiochem-BRL, San Diego, Calif., USA) according to the supplier's protocol. 5'-nucleotidase was assayed as the rate of production of inorganic phosphate from 5'-ANP (Emmelot et al., supra.).

Transfer of intracellular FC to the cell surface

This assay utilized the finding (see Example 1) that only FC in the caveolar fraction of the plasma membrane fraction was modified by cholesterol oxidase in unfixed fibroblast monolayers.

The rate at which intracellular LDL-derived $^3$H-FC became accessible at the cell surface was measured as follows. Cell monolayers were labeled with $^3$H-FC LDL under the conditions shown for each experiment. Unbound and adsorbed LDL were removed as described above. In some experiments metabolic inhibitors of different transport steps were then added for 30 min at 15° C. In each case, at the end of the experiment, the cells were washed with PBS containing recrystallized human serum albumin (5 mg ml$^{-1}$, pH 7.4) and then PBS. Cholesterol oxidase (Boehringer-Manheim, Indianapolis, Ind., USA) was added in PBS to a final concentration of 1 U ml$^{-1}$. Incubation was for 4 h at 0° C. The cells were washed with ice-cold PBS, and extracted with 0. 1N NAOH. Cell total lipid was extracted with chloroform-methanol (1:1 v/v). Thin-layer chromatography of portions of CHCl$_3$ phase was carried out on silica gel layers (Whatman PE Sil G, Fisher Scientific, Pittsburg, Pa., USA) developed in petroleum ether-diethyl ether-acetic acid 80/20/1 v/v. The yield of labeled cholest-4-en-3-one after 4 h at 0° C. did not differ significantly from that obtained after 1 h at 37° C., conditions shown earlier to completely oxidize FC in the caveolar membrane fraction (Smart et al., supra.).

Transfer of $^3$H-FCfrom LDL-effects of inhibitors

Horseradish peroxidase enters human fibroblasts exclusively by fluid phase endocytosis (Steinman etal., (1972) *J. Cell Biol.* 68: 665–687). Transferrin is internalized selectively via the clathrin-coated pits (Pearse & Robinson (1990) *Ann. Rev. Cell Biol.* 6: 151–172), while cholera toxin binds to ganglioside GMI localized to the caveolae (Montesano et al. (1982) *Nature*, 296: 651–653).

Internalization via clathrin-coated pits was selectively reduced by PBS made hyperosmotic by inclusion of 350 mM in place of 150 mM NaCl (Larkin et al., (1983) *Cell* 33: 273–285; Hansen et al. (1993) *J. Cell Biol.*, 121: 61–72; Cupers et al. (1994) *J. Cell Biol.*, 127: 725–735).

Figure 9:
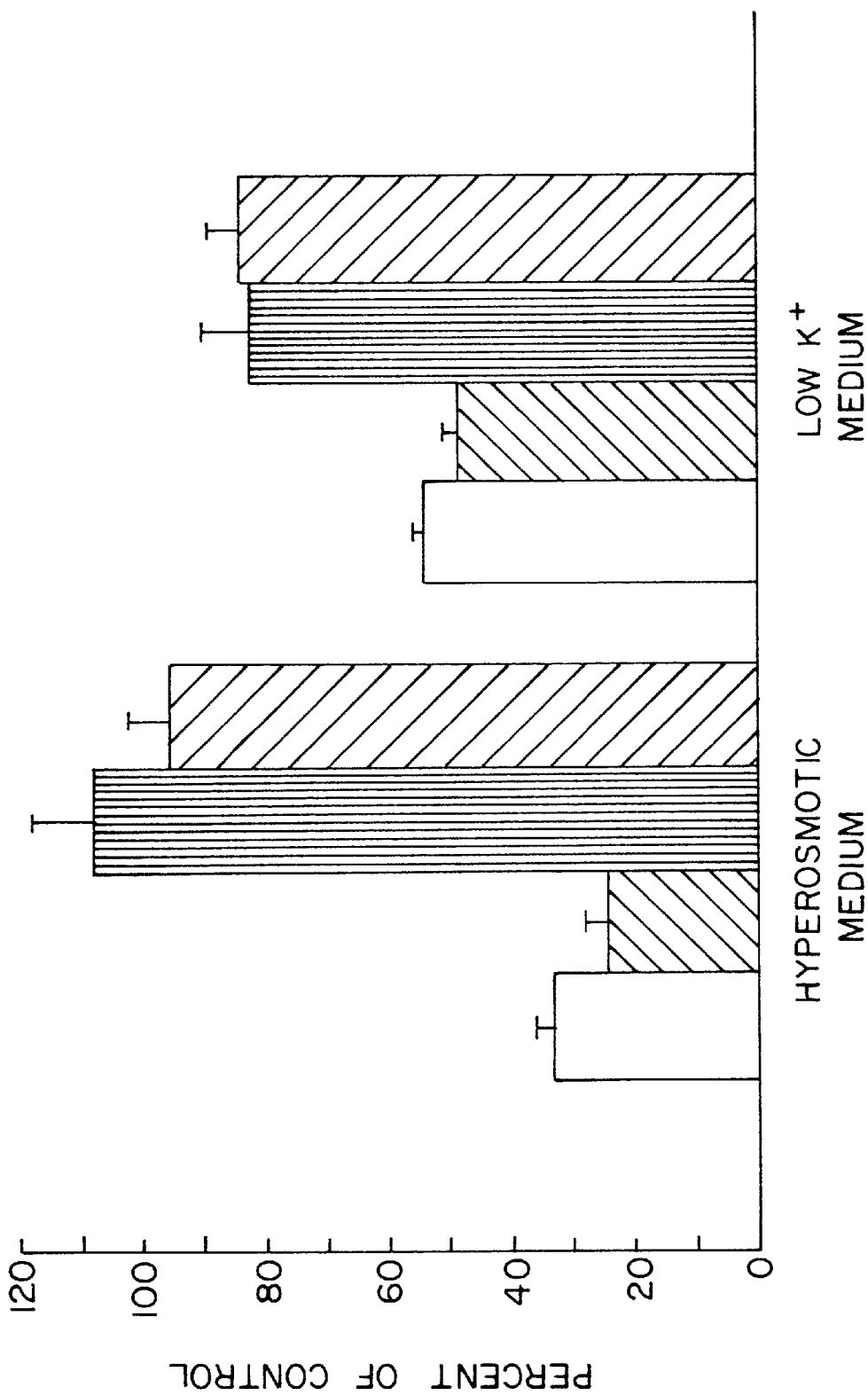
FIG. 9 illustrates uptake of $^3$H-LDL-FC, 125I-transferrin, $^{121}$I-cholera toxin or $^{121}$I-peroxidase by fibroblast monolayers incubated in hyperosmotic or K$^+$-free media. Monolayers were preincubated (60 min, 37° C.) with PBS or with hyperosmotic or K$^+$-free medium. Incubation was then carried out with $^3$H-labeled LDL or $^{125}$I-labeled transferrin or cholera toxin in the same media for 30 min. Incubation with $^{121}$I-peroxidase was for 5 min to minimize regurgitation of label. All rates were linear with time over the period of incubation. Cell-associated label in hyperosmotic or K$^+$-free media is expressed relative to the rate of uptake measured in PBS. Left to right for each panel: Open bars, $^3$H-FC LDL; diagonal bars, $^{121}$I-transferrin; vertical bars, $^{121}$I-peroxidase; black bars, $^{125}$I-cholera toxin.

The uptake of $^3$H-FC from LDL was significantly inhibited under these conditions (FIG. 9). A similar inhibition was observed with $^{125}$I-labeled transferrin. There was no significant reduction in the uptake of labeled peroxidase or cholera toxin by hyperosmotic medium. Endocytosis via clathrin-coated pits was also reduced in PBS in which K$^+$ was replaced isoosmotically by Na$^+$ (Cupers et al., supra.). The uptake of transferrin and $^3$H-FC from LDL was reduced comparably in K$^+$-free medium. There was no significant effect on the uptake of peroxidase or cholera toxin under these conditions (FIG. 9). Together the data indicate that the initial transfer of LDL-FC into the cell takes place via the coated pits.

Formation and subcellular fractionation of FC-labeled vesicles

The early stages of intracellular FC transport were studied by density-gradient centrifugation of cell homogenates, under conditions maximizing the formation of clathrin-coated vesicles (Woodman & Warren, supra.). These homogenates were obtained from fibroblast monolayers which had been incubated (2 h, 4° C.) with $^3$H-FC-LDL, then brought to 31° C. for 0.5 min.

Figure 10:
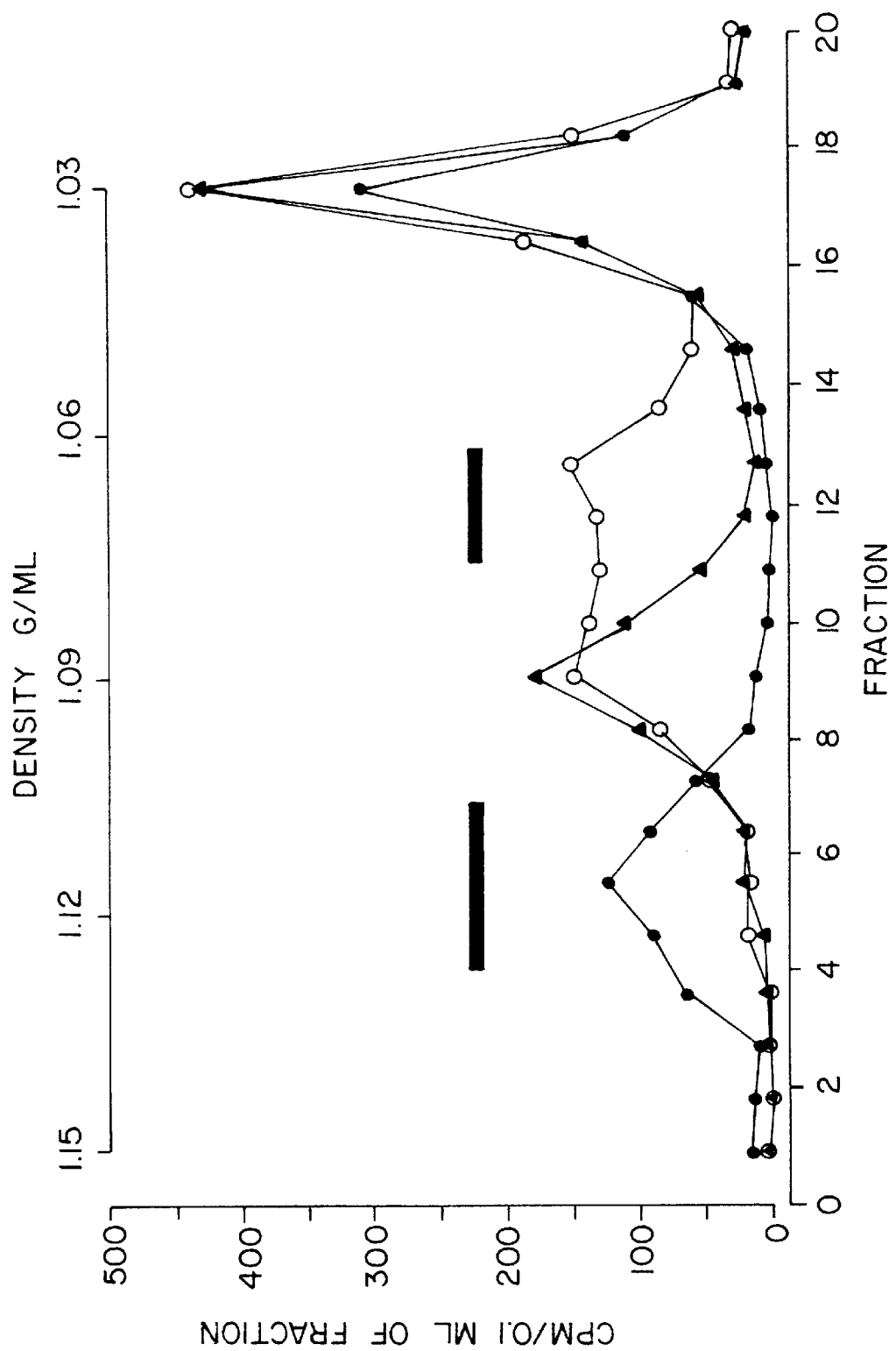
FIG. 10 shows the distribution of $^3$H-FC from LDL following D$_2$O-Ficoll density gradient centrifugation of fibroblast monolayers incubated with labeled LDL. Closed circles, incubation with $^3$H-FC LDL for 2 h at 4° C. then 0. 5 min at 31° C. in the absence of LDL. Open circles, the same, but with 2 min incubation at 31° C. in the absence of LDL. Closed triangles, the same, but with 15 min incubation at 31° C. in the absence of LDL. The distribution of $^{125}$I-transferrin is shown by solid bars. Greater than 95% of label was found within the fractions marked.

A peak of $^3$H-FC was recovered within the gradient at a density 1.12 g ml$^{-1}$ (fractions 4–6). The rest of the label was found at the top of the gradient (d 1.03 g ml$^{-1}$) (FIG. 10). A similar distribution was seen when the cells were incubated with 121I-transferrin, or when LDL-receptor-deficient (GN12000) cells replaced normal cells in reaction with $^3$HFC-labeled LDL. After 0.5 min, 74% of transferrin label within the gradient was recovered in the density 1.12 g ml$^{-1}$ fraction. 96% of clathrin was identified immunologically at d 1.12 g ml$^{-1}$ with the balance at the top of the gradient. Clathrin was undetectable in other fractions. Alkaline phosphatase, a GPI-anchored protein located in plasma membrane caveolae (Rothberg (1995) *Meth. Enzymol.* 250: 669–679) and 5'-nucleotidase, an additional marker for plasma membrane domains (Emmelot et al, supra.) were detected at the top of the gradient, but not elsewhere, under conditions where a 2% contaminant would have been detected. These data suggest that the initial appearance of $^3$H-FC label within the cell is in the clathrin-coated vesicles formed from cell-surface coated pits.

Effects of metabolic inhibitors on the uptake of LDL-FC

Several inhibitors reduce internalization of proteins through clathrin-coated pits (Pearse & Robinson, supra.). These agents were used initially at the highest concentrations described in the references cited below. Where inhibition was found, a concentration curve was obtained over at least a 10-fold concentration range. Cytochalasin inhibits endocytosis from coated pits, probably by preventing the polymerization of actin in microfilaments required for effective invagination (Gottlieb et al. (1993) *J. Cell Biol.* 120: 695–710). This agent reduced the uptake of $^3$H-FC from LDL by an average of 65% at 40 μM (Table 5). No greater inhibition was obtained at 100 μM.

TABLE 5

Transfer of LDL-derived 3H-FC into fibroblast monolayers in the presence and absence of metabolic inhibitors. Influx rates are means (±1 SD) from three experiments.

| Inhibitor | Concentration | Influx of 3H-FC % Remaining |
|---|---|---|
| None | — | 100 |
| Cytochalasin D | 40 μM | 38 ± 2 |
| Monensin | 40 μM | 39 ± 6 |
| Nocodazole | 60 μM | 101 ± 6 |
| Bafilomycin A1 | 45 μM | 70 ± 4 |

Monensin inhibits the endocytosis of intact LDL particles through the coated pits (Goldstein el aL (1985) *Ann. Rev. Cell Biol.* 1: 1–39). As shown in Table 5, it was also effective in reducing the selective uptake of FC from LDL. As with cytochalasin D, no increase in inhibition was found at concentrations up to 100 μM. Comparable results were obtained in LDL-receptor deficient (GM2000) cells.

Bafilomycin Al (45 μM), which inhibits ATPase-driven acidification of endocytic vesicles (Furuchi et al. (1993) *J. Biol. Chem.*, 268: 7345–7348) had a smaller maximal effect 30%) in these cells. Inhibitors of Golgi-mediated protein transport (brefeldin A, vinblastine, taxol) (Kristakis et al. (1992) *Nature*, 356: 344–346) were without effect at concentrations up to 60 μM on the uptake of $^3$H-FC from LDL, as was nocodazole (up to 60 μM), which inhibits microtubule-dependent transport under these conditions (Thyberg & Moskalewski (1992) *J. Cell Sci.*, 103: 1167–1175).

Intracellular transport of $^3$H-FC.

Fibroblast monolayers were labeled as before (2 h., 4° C.). Cell-surface and soluble LDL were removed. The dishes were then brought to 31° C. for 2 min in the absence of LDL. Density gradient ultracentrifugation, and determination of label distribution and solvent density, were carried out as described above. Most of the $^3$H-FC label had now disappeared from the d 1.12 g ml$^{-1}$ fraction. Label within the gradient was now in a light vesicle fraction (d 1.07 g ml$^{-1}$) (centered on fraction 12) with significant radioactivity in a fraction of intermediate density (d 1.09 g ml$^{-1}$) centered on fractions 9–10. Following more extended incubation in the absence of $^3$HFC LDL (up to 15 min at 31° C.) most of the label within the gradient became concentrated in the fraction of intermediate density. The distribution of FC was compared with that of transferrin, which in fibroblasts enters the cell exclusively via the clathrin coated pits (Woodman & Warren, supra. 1991).

$^{121}$I-transferrin label was also found in the light vesicle fraction (FIG. 10). In contrast to FC, none was found in the intermediate density fraction. Clathrin was not detected in either light or intermediate density fractions.

Under these conditions, the cellular origin of light and intermediate density fractions was investigated with antibodies to protein markers. The density of the light vesicles, the presence of $^{121}$I-transferrin and the absence of clathrin, suggested this fraction contained uncoated vesicles formed by the removal of clathrin by uncoating ATPase (Pearse & Robinson supra., Woodward & Warren supra.). This conclusion was strengthened by an apparent precursor-product relationship between the dense (1.12 g ml$^{-1}$) and light vesicles (d 1.07 g ml$^{-1}$).

In cells incubated with LDL as described above (15 min, 37° C.) the FC/phospholipid molar ratio of the light vesicle fraction was 0.42±0.02, while that of the intermediate density fraction was 0.65±0.03. The dense vesicle fraction (d 1.12 g ml$^{-1}$) had a FC/phospholipid molar ratio of 0.35±0.04, similar to the value of 0.30 reported for adrenal cell coated vesicles (Pearse (1976) *Proc. Natl. Acad Sci. USA* 73: 1255–1259). The FC/phospholipid ratio for the fraction (d 1.03 g ml$^{-1}$) containing the plasma membrane markers was 0.68±0.03, consistent with published data on this fraction (Cullis & Hope (1991) In *Biochemistry of Lipids, Lipoproteins and Membranes* (Vance, D. E. & Vance, J., Eds) pp 1–41, Elsevier Press, Amsterdam.). Under the same conditions, 75% of caveolin antigen was present in the intermediate density vesicle fraction. The balance was recovered with the plasma membrane markers at the top of the gradient.

The absence of $^{121}$I-transferrin from the intermediate density fraction (d 1.09 g ml$^{-1}$) suggested that transferrin and LDL-derived FC separated from each other in the endosomes, and returned to the cell surface by different pathways. This interpretation was also consistent with the kinetic data, which implied a precursor-product relationship between the light and intermediate-density fractions. Antibodies to different vesicle-bound proteins were used to obtain better identification of the intermediate density fraction.

Mannose 6-phosphate receptor protein is localized mainly to the trans-Golgi network (TGN) (Pfeffer (1991) *Cell Biophys.* 19: 131–140). Caveolin is present in the TGN as well as the plasma membrane (Dupree et al. (1993) *EMBO J.*, 12: 1597–1605) Both proteins are considered to recycle between the TGN and the cell surface. In cells preincubated (15 min) with $^3$H-FC LDL, 75% of caveolin antigen was recovered with the whole of detectable mannose 6-phosphate receptor protein in the intermediate density fraction. These data suggest that FC label in the intermediate density fraction comigrates during density gradient fractionation with vesicles derived from the TGN. The lack of any detectable alkaline phosphatase or 5'-nucleotidase activity in the intermediate density fraction argues against contamination with plasma membrane material.

To determine if exchange or diffusion during fractionation contributed to the changing distribution of FC label shown in FIG. 10, cells were labeled with $^3$H-FC from LDL. Fractionation of the cell homogenate was carried out by density gradient centrifugation as described above. Labeled fractions from the gradient were collected, mixed with homogenate from unlabeled cells, and recentrifuged as before. There was no significant redistribution of label. This finding indicates that the transfer of FC observed within the cell represents not an equilibration, but the orderly transport of this lipid between different cell compartments.

Effects of metabolic inhibitors on intracellular transport

N-ethylmaleimide (2 mM) blocks selective uptake of FC from LDL. In the presence of 2 mM NEM, no peak of FC label was present with clathrin at d 1.12 g ml$^{-1}$. Almost all was recovered with the plasma membrane fraction at the top of the gradient. A similar result was obtained in the presence of cytochalasin or monensin. The results indicate that these inhibitors of the selective transfer of LDL-FC into the cell inhibit the formation of clathrin-associated vesicles from the plasma membrane.

Return of intracellular FC to the cell surface.

Figure 11:
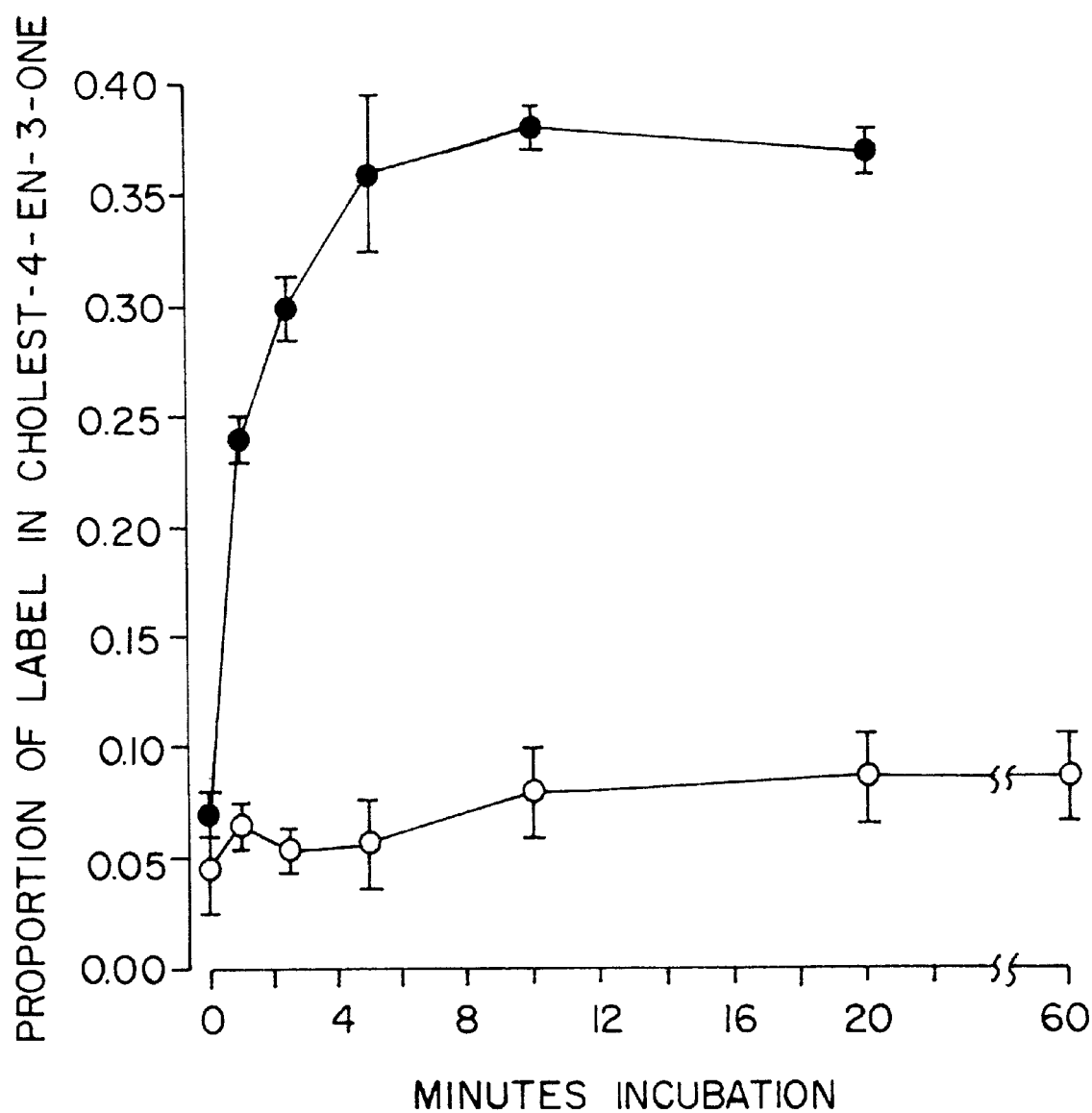
FIG. 11 shows the rate of transfer of $^3$H-FC to the cell surface as a function of temperature. Cell monolayers were prelabeled (2 min, 31° C.) with labeled LDL. Noninteriorized LDL was removed as described in Example 2. The cells were then incubated in the absence of LDL at either 15 or 31° C. for the period indicated. The cells were then cooled on ice, and incubated with cholesterol oxidase (1 U ml$^{-1}$) for 4 h. The oxidized fraction of FC is expressed as a percent of total label. Open circles, 15° C., closed circles, 31° C.

In preliminary studies, fibroblast monolayers were pulse-labeled (2 min, 31° C.) with $^3$H-FC transferred from LDL. The cells were then washed, and surface-bound labeled LDL displaced, as described above. The cells were incubated with cholesterol oxidase at 0–4° C., and the oxidized fraction of FC determined as a fraction of total FC label (Smart et al. supra.). Under these conditions, the cholest-4-en-3-one fraction represented less than 1% of total label (4 experiments, 0.8±0.2%). This result indicates that little or no $^3$H-FC moves through the cell into the caveolae at 4° C. Other cells labeled in the same way were brought to 15° C. for up to 60 min before incubation with cholesterol oxidase at 0–4° C. There was only a slight increase in the amount of cell-surface FC label accessible to cholesterol oxidase (FIG. 11). In contrast, when incubation was carried out at 31° C., there was a rapid increase in oxidized FC ($t_{1/2}$~2 min) reflecting the transfer of FC label from intracellular pools to the cell surface. Following the 2 min pulse label, about 40% of internalized FC became eventually localized to the oxidase-sensitive fraction, a proportion approximately ten-fold higher than that of cellular FC in this fraction in unloaded cells.

Figure 12:
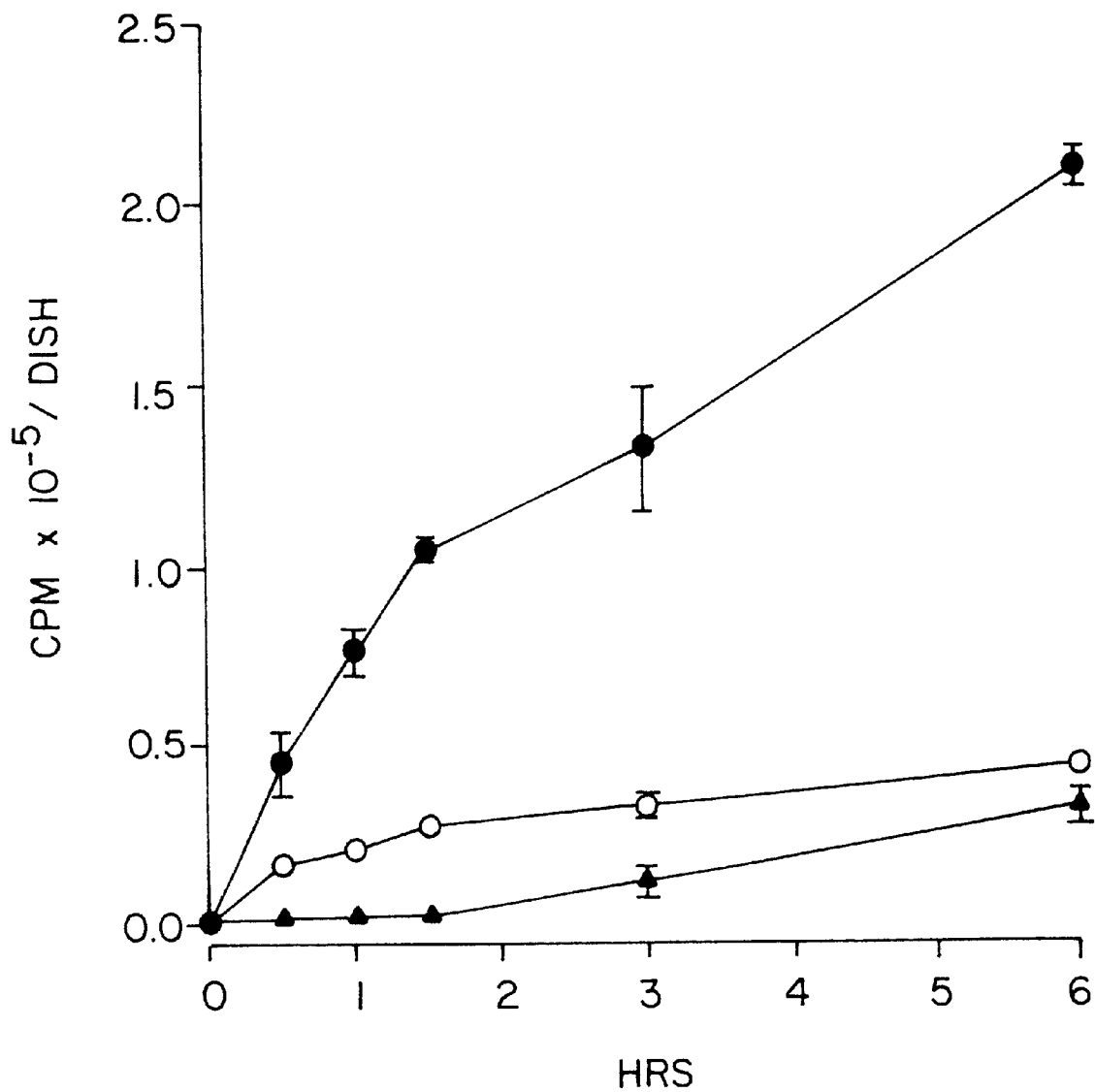
FIG. 12 illustrates evidence of the saturation of the caveolar FC compartment. Cells were incubated at 31° C. with $^3$H-FC-labeled LDL. At the intervals shown, cells were cooled on ice, and intact LDL particles removed as described in Example 2. Cholesterol oxidase (1 U ml$^{-1}$) was added for 4 h at 4° C. The level of label in cholesterol ester (CE), free cholesterol (FC) and cholest-5-en-4-one was then determined following thin-layer chromatography as described in Example 2. Open circles, cholest-4-en-3-one; closed circles, FC; closed triangles CE.

In other experiments, cells were continuously labeled with $^3$H-FC LDL at 31° C. in the absence of medium HDL, for a period of up to 60 min. Under these conditions FC accumulates in the cell. At intervals monolayers were cooled on ice, medium and cellsurface LDL removed, and the washed cells incubated at 0–4° C. with cholesterol oxidase. Oxidase-accessible FC was nearly maximal after approximately 60 min at 37° C. Total cell label (mainly unoxidized FC) continued to increase (FIG. 12). FC label accumulated in an intracellular compartment not accessible to cholesterol oxidase. As shown above, the intracellular (oxidase-inaccessible) label under these conditions is recovered as a single major peak in the intermediate density fraction.

Fibroblast monolayers were prelabeled with FC-labeled LDL for 2 min at 31° C. Medium and surface-bound labeled LDL were removed as described above. The cells were incubated with inhibitors of intracellular transport for 30 min at 15° C. Movement of FC label to the cell surface remained negligible (FIG. 11). The cells were brought to 31° C. for 15 min, and then cooled on wet ice. $^3$H-FC transfer to the cell surface (in the presence and absence of inhibitor) was assayed with cholesterol oxidase as described above.

The transport of intracellular $^3$H-FC to the cell surface was reduced by nocodazole (Table 6). It was unaffected by vinblastine and by brefeldin A, which inhibit transport from the Golgi stacks but has little reported effect on vesicular transport from the TGN (Chege & Pfeffer (1990) *J. Cell Biol*, 1: 893–899). There was no effect of cytochalasin D or monensin on transport to the caveolae under conditions that inhibited initial uptake of FC from LDL (Table 5). N-ethyl maleimide and NO$_3$ inhibitors of vesicle ATPases, which inhibited the initial endocytosis of LDL-FC, also inhibited the return of FC to the cell surface, but less effectively than did nocodazole.

TABLE 6

Effects of metabolic inhibitors on the rate of transfer of intracellular $^3$H-FC to the cell surface.

| Inhibitor | Concentration | % transfer[a] |
|---|---|---|
| N-ethyl maleimide | 2 mM | 50 ± 3 |
| KNO$_3$ | 50 mM | 70 ± 4 |
| Nocodazole | 40 µM | 40 ± 1 |
| Brefeldin A | 40 µM | 95 ± 5 |
| Vinblastine | 40 µM | 100 ± 2 |

[a]Relative to rate in the absence of inhibitor. Values are expressed in terms of 3H-FC oxidized to cholest-5-en-4-one by cholesterol oxidase (1 U ml$^{-1}$, 4 h at 0° C.) with cells pulse labeled with labeled LDL (2 min 31° C.) then incubated without LDL for 30 min (31° C.) in the presence of individual inhibitors. Data are from triplicates of individual dishes expressed as a percent of oxidized label recovered in the absence of inhibitor.

Effect of medium lipoproteins on the distribution of intracellular FC

Figure 13:
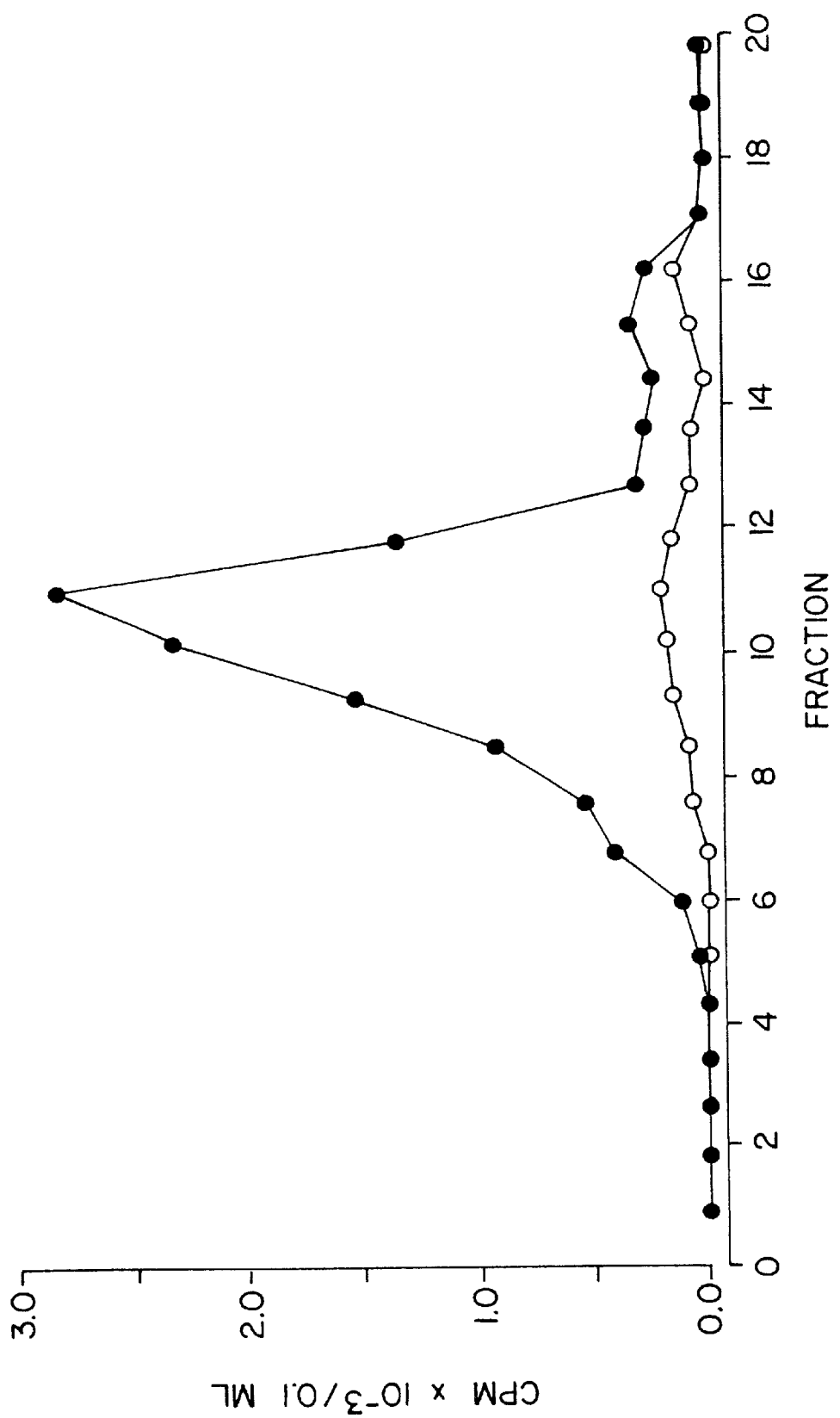
FIG. 13 illustrates the unloading of LDL-derived FC to the extracellular medium in the presence of native plasma. Labeling of the cells was carried out as described in Example 2. The labeled cells were then incubated with plasma or PBS for 5 min at 31° C. The cells were then cooled on ice, homogenized, and fractionated by D$_2$O-Ficoll gradient. Closed circles, distribution after incubation in the presence of PBS; open circles, distribution in the presence of plasma.

Fibroblast monolayers were incubated with $^3$H-FC LDL for 30 min at 31° C. to predominantly label the intermediate density vesicle fraction. Cell surface LDL was removed as described above. The cells were then incubated (5 min, 31° C.) in the presence of human plasma or PBS. In the cells exposed to plasma there was a 12-fold decrease in the intermediate density fraction (FIG. 13). There was a smaller decrease in the plasma membrane fraction. Since relatively little of total cell label was at the cell surface under these conditions (FIG. 12), these data indicate that label in the intermediate density fraction can be quickly unloaded to the extracellular medium. It was shown above that FC was rapidly unloaded from these cells through the caveolae. Consequently, FC in the intermediate density fraction must be transferred to the caveolae prior to unloading.

Intracellular transport of LDL-derived free cholesterol

Cell-surface clathrin-coated pits are the portal by which many receptor-bound proteins enter the cell. The selective uptake of FC from LDL takes place without the internalization of LDL protein. Nevertheless, the results of this study are consistent in indicating that selective FC transfer is also initiated via coated pits. Interalization of FC, like that of transferrin (Pearse & Robinson supra.) was reduced by hyperosmotic and K$^+$-deficient media. Reduced FC uptake was also observed with other inhibitors of receptor-mediated endocytosis, including monensin and cytochalasin. Finally, LDL-derived FC was recovered in the same density gradient fraction as $^{121}$I-transferrin and clathrin; and the appearance of label in these peaks was blocked by inhibitors along with selective FC transfer into the cell. The mechanism by which FC enters coated pits selectively from LDL must be distinct from that involving the high affinity LDL receptor, since the rate of FC transfer is normal in LDL-receptor deficient (GM2000) cells. The FC/phospholipid ratio of isolated coated vesicles in this study was relatively low, compared to that of whole plasma membrane fraction or LDL itself (Fielding & Fielding (1986) *J. Biol. Chem.*, 261: 5233–5236) consistent with earlier data (Pearse supra.). It is possible that FC transfers spontaneously to the outer leaflet of the coated pits, and could help trigger the budding of the endocytic vesicle. The selective uptake of FC may be most relevant in cells where LDL receptors are mainly downregulated.

Vesicles formed from clathrin-coated pits are converted rapidly to a light vesicle fraction through the action of uncoating ATPase (Rothman & Schmit (1986) *Cell*, 46: 5–9). The endosomal contents are retained in the vesicle. The first appearance of $^{121}$I-transferrin and H-FC in a light (d 1.07 g ml$^{-1}$) fraction is consistent with the expected kinetics of this conversion (Woodman & Warren supra.). Shortly thereafter, FC and transferrin separated into different compartments. FC but not transferrin moved to an intermediate density fraction and finally appeared in a plasma membrane fraction enriched in caveolin. Transferrin (but not FC) was retumed to a non-caveolar domain of the cell surface. Earlier studies showed that FC selectively internalized from LDL became briefly inaccessible, before reappearing in the plasma membrane caveolae fraction, from which it could be released by HDL. These new data suggest that as part of this transport process, FC transits through a vesicle fraction of intermediate density.

Several pieces of evidence now suggest that the TGN may be a significant component of this fraction. The mannose 6-phosphate receptor protein, identified in the intermediate density fraction, is present mainly in the TGN (Pfeffer supra.). Caveolin, present mainly in the intermediate density fraction in this study as well as in the plasma membranes, has been previously recognized as a protein component of the TGN (Dupree et al. supra.). Caveolin is believed to migrate between the TGN and cell-surface caveolae (Conrad et al. (1995) *J. Cell Biol.* 131, 1421–1433), at least partially in response to cellular FC levels (Smart et al., supra.). Consistent with this relationship, the TGN was identified by electron microscopy in filipin-treated cells as the most FC-rich component of the Golgi stack (Coxey et al. (1993) *J. Lipid Res.*, 34: 1165–1176). In the present study, the FC/phospholipid ratio of the intermediate density vesicle fraction was higher than that of primary endocytic vesicles, and similar to that of the plasma membrane fraction. It was recently suggested that FC may play an important role in regulating the sorting activities of the Golgi apparatus, with the lowest levels of FC (relative to phospholipid) in the cisGolgi vesicles and the highest in the lrans-Golgi and TGN (Bretscher & Munro (1993) *Science* 261: 1280–1281).

The above data are consistent with a model in which the intermediate density fraction, which colocalizes with material from the TGN on density gradients, represents a component of the intracellular transport of LDL-derived FC, and a reservoir from which excess FC can be transferred to the caveolae for release to plasma lipoproteins, particularly HDL.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method of identifying an agent that blocks or enhances the transport of free cholesterol from the plasma membrane to a cholesterol transport vesicle, said method comprising:

contacting said cell with said agent in the presence of low-density lipoprotein; and quantifying the amount of free cholesterol internalized from said LDL by said cell, wherein said uptake is selective and almost unaccompanied by the uptake of LDL protein.

2. The method of claim 1, wherein said low-density lipoprotein comprises a labeled cholesterol.

3. The method of claim 2, wherein said quantifying comprises detecting said labeled cholesterol in said cell.

4. The method of claim 1, wherein said quantifying comprises quantifying the amount of a cholesterol transport vesicle produced by said cell.

5. The method of claim 1, wherein said cell is selected from the group consisting of a fibroblast, a vascular smooth muscle cell, a vascular endothelial cell, a macrophages, a hematopoietic cell, a liver cell, a kidney cell, and an intestinal mucosal cell.

6. The method of claim 2, wherein said labeled low-density lipoprotein comprises a [$^3$H]-free cholesterol.

7. A method of detecting abnormal lipid uptake by a cell, said method comprising the steps of:

placing said cell in media comprising known concentrations of high-density lipoprotein (HDL) and low-density lipoprotein (LDL); and quantifying the uptake of free cholesterol from said LDL by said cell wherein said uptake is selective and almost unaccompanied by the uptake of LDL protein.

8. The method of claim 7, wherein said low-density lipoprotein comprises a labeled cholesterol.

9. The method of claim 8, wherein said quantifying comprises detecting said labeled cholesterol in said cell.

10. The method of claim 8, wherein said labeled low-density lipoprotein comprises a [$^3$H]-free cholesterol.

11. The method of claim 7, wherein said quantifying comprises quantifying the amount of a cholesterol transport vesicle produced by said cell.

12. The method of claim 7, wherein said cell is selected from the group consisting of a fibroblast, a vascular smooth muscle cell, a vascular endothelial cell, a macrophages, a hematopoietic cell, a liver cell, a kidney cell, and an intestinal mucosal cell.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 15 amino acids
      (B) TYPE: amino acid
      (C) STRANDEDNESS:
      (D) TOPOLOGY: linear (ii) MOLECULE TYPE: peptide (ix) FEATURE:
      (A) NAME/KEY: Region
      (B) LOCATION: 1..15
      (D) OTHER INFORMATION: /note= "ATP binding region from
          position 265 to 279 in the ATPase
          N-ethylmaleimide-sensitive protein
      (NSF)"

(xi) SEQUENCE DESCRIPTION: SEQ ID NO:1:

Leu Leu Tyr Gly Pro Pro Gly Cys Gly Lys Thr Leu Leu Ala Arg
   1            5                  10               15

(2) INFORMATION FOR SEQ ID NO:2:

(i) SEQUENCE CHARACTERISTICS:
      (A) LENGTH: 15 amino acids
      (B) TYPE: amino acid
      (C) STRANDEDNESS:
      (D) TOPOLOGY: linear (ii) MOLECULE TYPE: peptide (ix) FEATURE:
      (A) NAME/KEY: Region
      (B) LOCATION: 1..15
      (D) OTHER INFORMATION: /note= "ATP binding region from
          position 515 to 529 in the ATPase
          valosin-containing protein (VCP)"

(xi) SEQUENCE DESCRIPTION: SEQ ID NO:2:

Leu Phe Tyr Gly Pro Pro Gly Cys Gly Lys Thr Leu Leu Ala Lys
   1            5                  10               15